US010433728B2

(12) United States Patent
Kuo

(10) Patent No.: US 10,433,728 B2
(45) Date of Patent: Oct. 8, 2019

(54) MEDICAL IMAGING SYSTEM FOR DETERMINING A SCAN ORIENTATION

(71) Applicant: Yu-Ching Audrey Kuo, Toronto (CA)

(72) Inventor: Yu-Ching Audrey Kuo, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 15/736,842

(22) PCT Filed: Jun. 19, 2015

(86) PCT No.: PCT/IB2015/054642
§ 371 (c)(1),
(2) Date: Dec. 15, 2017

(87) PCT Pub. No.: WO2016/203295
PCT Pub. Date: Dec. 22, 2016

(65) Prior Publication Data
US 2018/0360316 A1 Dec. 20, 2018

(51) Int. Cl.
*A61B 5/00* (2006.01)
*A61B 34/10* (2016.01)
(Continued)

(52) U.S. Cl.
CPC ............ *A61B 5/0037* (2013.01); *A61B 5/055* (2013.01); *A61B 5/0555* (2013.01); *A61B 5/749* (2013.01);
(Continued)

(58) Field of Classification Search
CPC ............ G06T 7/0012; G06T 2219/028; G06T 2207/10088; G06T 2219/2016; G06T 7/33;
(Continued)

(56) References Cited

U.S. PATENT DOCUMENTS

| 8,334,867 | B1* | 12/2012 | Davidson | ............ G06F 3/04815 345/419 |
| 2005/0122343 | A1* | 6/2005 | Bailey | ............ G06T 3/0037 345/619 |
| 2007/0249934 | A1* | 10/2007 | Aksit | ............ A61B 5/055 600/427 |
| 2008/0071163 | A1* | 3/2008 | Zhang | ............ A61B 5/055 600/410 |

(Continued)

FOREIGN PATENT DOCUMENTS

| CA | 2904766 A1 | 9/2014 |
| CA | 2906414 A1 | 9/2014 |

OTHER PUBLICATIONS

International Search Report, dated Jan. 19, 2016, PCT/IB2015/054642.

*Primary Examiner* — Jingge Wu
(74) *Attorney, Agent, or Firm* — Perry + Currier Inc.

(57) ABSTRACT

A medical imaging system for determining a scan orientation is provided. The system comprises: a computing device; a display device; an input device; and, an imaging device, the computing device configured to: instruct the imaging device to acquire at least a sagittal scout scan, an axial scout scan and a coronal scout scan, based on an initial frame of reference; render, at the display device: a two-dimensional representation of each of the scout scans and initial respective selections of a portion of each of the scout scans, oriented according to the initial frame of reference; receive, from the input device, a respective reorientation of one or more of the initial respective selections; transform the initial frame of reference using the respective to produce a reoriented frame of reference; and, instruct the imaging device to acquire further images based on the reoriented frame of reference.

24 Claims, 17 Drawing Sheets

(51) Int. Cl.
*A61B 6/03* (2006.01)
*A61B 6/00* (2006.01)
*A61B 5/055* (2006.01)
*G01R 33/54* (2006.01)

(52) U.S. Cl.
CPC .......... *A61B 5/7425* (2013.01); *A61B 5/7435* (2013.01); *A61B 6/032* (2013.01); *A61B 6/037* (2013.01); *A61B 6/463* (2013.01); *A61B 6/465* (2013.01); *A61B 6/466* (2013.01); *A61B 6/467* (2013.01); *A61B 6/469* (2013.01); *A61B 6/488* (2013.01); *A61B 6/5223* (2013.01); *A61B 6/545* (2013.01); *A61B 34/10* (2016.02); *G01R 33/543* (2013.01); *G01R 33/546* (2013.01); *A61B 5/0066* (2013.01); *A61B 2576/00* (2013.01)

(58) Field of Classification Search
CPC . G06T 2207/10081; G06T 2207/10132; A61B 2034/108; A61B 2034/105; A61B 34/10; A61B 34/20; A61B 5/055; A61B 5/0037; A61B 6/032; A61B 5/749; A61B 5/7435; A61B 5/0555; A61B 5/7425; A61B 6/463; A61B 6/465–467; A61B 6/469; A61B 6/388; A61B 6/037; A61B 5/065; A61B 5/1076; A61B 8/0833
See application file for complete search history.

(56) References Cited

U.S. PATENT DOCUMENTS

| | | | | |
|---|---|---|---|---|
| 2009/0093706 | A1* | 4/2009 | Zhang | A61B 5/055 600/410 |
| 2012/0093385 | A1* | 4/2012 | Yokosawa | A61B 5/0037 382/131 |
| 2014/0055456 | A1* | 2/2014 | Holthuizen | G06T 19/003 345/424 |
| 2014/0111508 | A1* | 4/2014 | Bystrov | G06F 19/321 345/419 |
| 2014/0134586 | A1* | 5/2014 | Stein | G09B 23/28 434/262 |
| 2014/0135773 | A1* | 5/2014 | Stein | G06F 19/00 606/80 |
| 2014/0191756 | A1* | 7/2014 | Yokosawa | A61B 5/055 324/318 |
| 2014/0270434 | A1* | 9/2014 | Gulaka | G01R 33/543 382/128 |
| 2014/0303486 | A1* | 10/2014 | Baumgartner | A61B 5/055 600/414 |
| 2015/0109427 | A1* | 4/2015 | Wood | A61B 1/043 348/68 |
| 2015/0351860 | A1* | 12/2015 | Piron | A61B 5/0095 600/417 |
| 2015/0366620 | A1* | 12/2015 | Cameron | A61B 17/3421 606/130 |
| 2016/0078615 | A1* | 3/2016 | Zhan | G06T 7/11 382/128 |
| 2016/0155247 | A1* | 6/2016 | Robinson | A61B 8/4254 382/131 |

* cited by examiner

MEDICAL IMAGING SYSTEM FOR DETERMINING A SCAN ORIENTATION

FIELD

The specification relates generally to medical imaging, and, in particular, a medical imaging system for determining a scan orientation.

BACKGROUND

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimes, and radiation therapy are only a few examples of procedures utilizing imaging guidance in the medical field.

Advanced imaging modalities such as Magnetic Resonance Imaging ("MRI") have led to improved rates and accuracy of detection, diagnosis and staging in several fields of medicine including neurology, where imaging of diseases such as brain cancer, stroke, Intra-Cerebral Hemorrhage ("ICH"), and neurodegenerative diseases, such as Parkinson's and Alzheimer's, are performed. As an imaging modality, MRI enables three-dimensional visualization of tissue with high contrast in soft tissue without the use of ionizing radiation. This modality is often used in conjunction with other modalities such as Ultrasound ("US"), Positron Emission Tomography ("PET") and Computed X-ray Tomography ("CT"), by examining the same tissue using the different physical principals available with each modality. CT is often used to visualize boney structures, and blood vessels when used in conjunction with an intra-venous agent such as an iodinated contrast agent. Vascular visualization may also be acquired by MRI using a contrast agent, such as an intra-venous gadolinium based contrast agent which has pharmaco-kinetic properties that enable visualization of tumors (in some instances), and break-down of the blood brain barrier. These multi-modality solutions may provide varying degrees of contrast between different tissue types, tissue function, and disease states. Imaging modalities may be used in isolation, or in combination to better differentiate and diagnose disease.

Patient positioning is often the most time-consuming aspect of setting up for an imaging study, including MRI studies. For example, it is desirable to align the patient anatomy as much as possible to the imaging device (e.g. scanner) frame of reference. This is analogous to the way a map is aligned to a compass when way finding in the physical world. However, due to patient comfort and other factors, such as the way external equipment is attached, and/or how a patient is anchored to a scanning bed, alignment of patient anatomy to the imaging device frame of reference is not always possible. In particular, a patient is positioned in their most comfortable position to minimize patient movement during a scan. Even when in an interpretative situation, where a patient may be sedated, optimal positioning may be limited because of a site of a surgery and the way patient was optimized for the surgical position.

As a result, it is often necessary to provide instructions to the imaging device/scanner on a desirable scan orientation based on the way patient is positioned. This way, the imaging device/scanner may adjust its magnetic gradient (e.g. for an MRI) accordingly during image acquisition and provide an output of the anatomy that is oriented in a clinically relevant way. For example, instead of a typical supine or prone position, the patient maybe positioned in a lateral recumbent position with their head rotated in a way that is optimized for a surgical access to the lateral side of their head. If the patient is scanned without adjustment to the scan orientation, the scanner will make assumption about the right, left, anterior, posterior, superior, inferior direction and output misleading directional information on the resulting image. In the less severe case where the patient is aligned closely to the scanner frame of reference, clinicians would still like to conveniently make adjustment to the scan orientation so that the internal anatomy appears as similar to textbook anatomy as is possible.

SUMMARY

The present specification is directed to a medical imaging system for determining a scan orientation in which a computing device. In particular, the present specification provides a medical imaging system for determining a scan orientation, the medical imaging system comprising: a computing device comprising a processor, a communication interface and a memory; a display device; an input device configured to provide interactions with the display device; and, an imaging device configured to acquire digital images, the computing device configured to communicate with the display device and the imaging device using the communication interface, the processor configured to: instruct the imaging device to acquire at least a sagittal scout scan, an axial scout scan and a coronal scout scan, based on an initial frame of reference, the initial frame of reference based on one or more of the imaging device and a patient located in the imaging device; render, at the display device: a two-dimensional representation of each of the sagittal scout scan, the axial scout scan and the coronal scout scan; render, at the display device, initial respective selections of a portion of each of the sagittal scout scan, the axial scout scan and the coronal scout scan, oriented according to the initial frame of reference, the initial respective selections representing an initial field of view of an acquisition volume of the imaging device, the initial respective selections being automatically selected according to the initial frame of reference; receive, from the input device, input indicating a respective reorientation of one or more of the initial respective selections; transform the initial frame of reference using the respective reorientation of one or more of the respective initial respective selections to produce a reoriented frame of reference; and, instruct the imaging device to acquire further images based on the reoriented frame of reference. The processor may comprise a hardware processor.

The processor may be further configured to instruct the imaging device to acquire at least the sagittal scout scan, the axial scout scan and the coronal scout scan by instructing the imaging device to acquire a three-dimensional scout scan based on the initial frame reference. The processor may be further configured to extract the two-dimensional representation of each of the sagittal scout scan, the axial scout scan and the coronal scout scan from the three-dimensional scout scan. The processor may be further configured to: process the three-dimensional scout scan to produce a cut-out view; and render, at the display device, the cut-out view combined with a three-dimensional volume representation of the acquisition volume.

The processor may be further configured to instruct the imaging device to acquire at least the sagittal scout scan, the axial scout scan and the coronal scout scan by instructing the imaging device to acquire a two-dimensional sagittal scout scan, a two-dimensional axial scout scan and a two-dimensional coronal scout scan.

The medical imaging system may further comprise a device configured to acquire a patient frame of reference of the patient located in the imaging device, the processor in communication with the device, and the initial frame of reference may be based on the patient frame of reference.

The automatically selected initial respective selections of a portion of each of the sagittal scout scan, the axial scout scan and the coronal scout scan may comprise at least one three-dimensional selection.

Instructions for acquiring the further images may comprise instructions for acquiring a three-dimensional image oriented according to the reoriented frame of reference.

The initial respective selections may comprise respective rectangles overlaid on each of the sagittal scout scan, the axial scout scan and the coronal scout scan. The respective rectangles may again be rendered, at the display device, when input indicating the respective reorientation of one or more of the initial respective selections is received.

The input device may comprise one or more of: a touchscreen at the display device, a mouse, a rotatable mouse, a foot pedal, a microphone configured to receive voice commands, and a gesture-based input device.

The imaging device may comprise a magnetic resonance imaging system, and the processor may be further configured to instruct the imaging device to acquire the further images by instructing the imaging device to align magnetic gradients with the reoriented frame of reference.

The processor may be further configured to render, at the display device, a three-dimensional volume representation of the acquisition volume based on the respective reorientation of one or more of the initial respective selections.

Another aspect of the specification provides a method for determining a scan orientation, in a medical imaging system, the method comprising: at the medical imaging system comprising: a computing device comprising a processor, a communication interface and a memory; a display device; an input device configured to provide interactions with the display device; and, an imaging device configured to acquire digital images, the computing device configured to communicate with the display device and the imaging device using the communication interface: instructing, at the processor, the imaging device to acquire at least a sagittal scout scan, an axial scout scan and a coronal scout scan, based on an initial frame of reference, the initial frame of reference based on one or more of the imaging device and a patient located in the imaging device; rendering, at the display device: a two-dimensional representation of each of the sagittal scout scan, the axial scout scan and the coronal scout scan; rendering, at the display device, initial respective selections of a portion of each of the sagittal scout scan, the axial scout scan and the coronal scout scan, oriented according to the initial frame of reference, the initial respective selections representing an initial field of view of an acquisition volume of the imaging device, the initial respective selections being automatically selected according to the initial frame of reference; receiving, at the processor, from the input device, input indicating a respective reorientation of one or more of the initial respective selections; transforming, at the processor, the initial frame of reference using the respective reorientation of one or more of the respective initial respective selections to produce a reoriented frame of reference; and, instructing, at the processor, the imaging device to acquire further images based on the reoriented frame of reference. The processor may comprise a hardware processor.

The method may further comprise instructing, at the processor, the imaging device to acquire at least the sagittal scout scan, the axial scout scan and the coronal scout scan by instructing the imaging device to acquire a three-dimensional scout scan based on the initial frame reference. The method may further comprise extracting, at the processor, the two-dimensional representation of each of the sagittal scout scan, the axial scout scan and the coronal scout scan from the three-dimensional scout scan. The method may further comprise: processing, at the processor, the three-dimensional scout scan to produce a cut-out view; and rendering, at the display device, the cut-out view combined with a three-dimensional volume representation of the acquisition volume.

The method may further comprise instructing, at the processor, the imaging device to acquire at least the sagittal scout scan, the axial scout scan and the coronal scout scan by instructing the imaging device to acquire a two-dimensional sagittal scout scan, a two-dimensional axial scout scan and a two-dimensional coronal scout scan.

The medical imaging system may further comprise a device configured to acquire a patient frame of reference of the patient located in the imaging device, the processor in communication with the device, and the initial frame of reference may be based on the patient frame of reference.

The automatically selected initial respective selections of a portion of each of the sagittal scout scan, the axial scout scan and the coronal scout scan may comprise at least one three-dimensional selection.

Instructions for acquiring the further images may comprise instructions for acquiring a three-dimensional image oriented according to the reoriented frame of reference.

The initial respective selections may comprise respective rectangles overlaid on each of the sagittal scout scan, the axial scout scan and the coronal scout scan. The respective rectangles may again rendered, at the display device, when input indicating the respective reorientation of one or more of the initial respective selections is received.

The imaging device may comprise a magnetic resonance imaging system, and the method may further comprise: instructing, at the processor, the imaging device to acquire the further images by instructing the imaging device to align magnetic gradients with the reoriented frame of reference.

The method may further comprise rendering, at the display device, a three-dimensional volume representation of the acquisition volume based on the respective reorientation of one or more of the initial respective selections.

Another aspect of the specification provides a computer-readable medium storing a computer program, wherein execution of the computer program is for: at a medical imaging system comprising: a computing device comprising a processor, a communication interface and a memory; a display device; an input device configured to provide interactions with the display device; and, an imaging device configured to acquire digital images, the computing device configured to communicate with the display device and the imaging device using the communication interface: instructing, at the processor, the imaging device to acquire at least a sagittal scout scan, an axial scout scan and a coronal scout scan, based on an initial frame of reference, the initial frame of reference based on one or more of the imaging device and a patient located in the imaging device; rendering, at the display device: a two-dimensional representation of each of the sagittal scout scan, the axial scout scan and the coronal scout scan; rendering, at the display device, initial respective selections of a portion of each of the sagittal scout scan, the axial scout scan and the coronal scout scan, oriented according to the initial frame of reference, the initial respective selections representing an initial field of view of an acquisition volume of the imaging device, the initial respective selections being automatically selected according to the initial frame of reference; receiving, at the processor, from the input device, input indicating a respective reorientation of one or more of the initial respective selections; transforming, at the processor, the initial frame of reference using the respective reorientation of one or more of the respective initial respective selections to produce a reoriented frame of reference; and, instructing, at the processor, the imaging device to acquire further images based on the reoriented frame of reference. The computer-readable medium may comprise a non-transitory computer-readable medium

BRIEF DESCRIPTIONS OF THE DRAWINGS

Embodiments will now be described, by way of example only, with reference to the drawings, in which.

DETAILED DESCRIPTION OF THE EMBODIMENTS

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Figure 1:
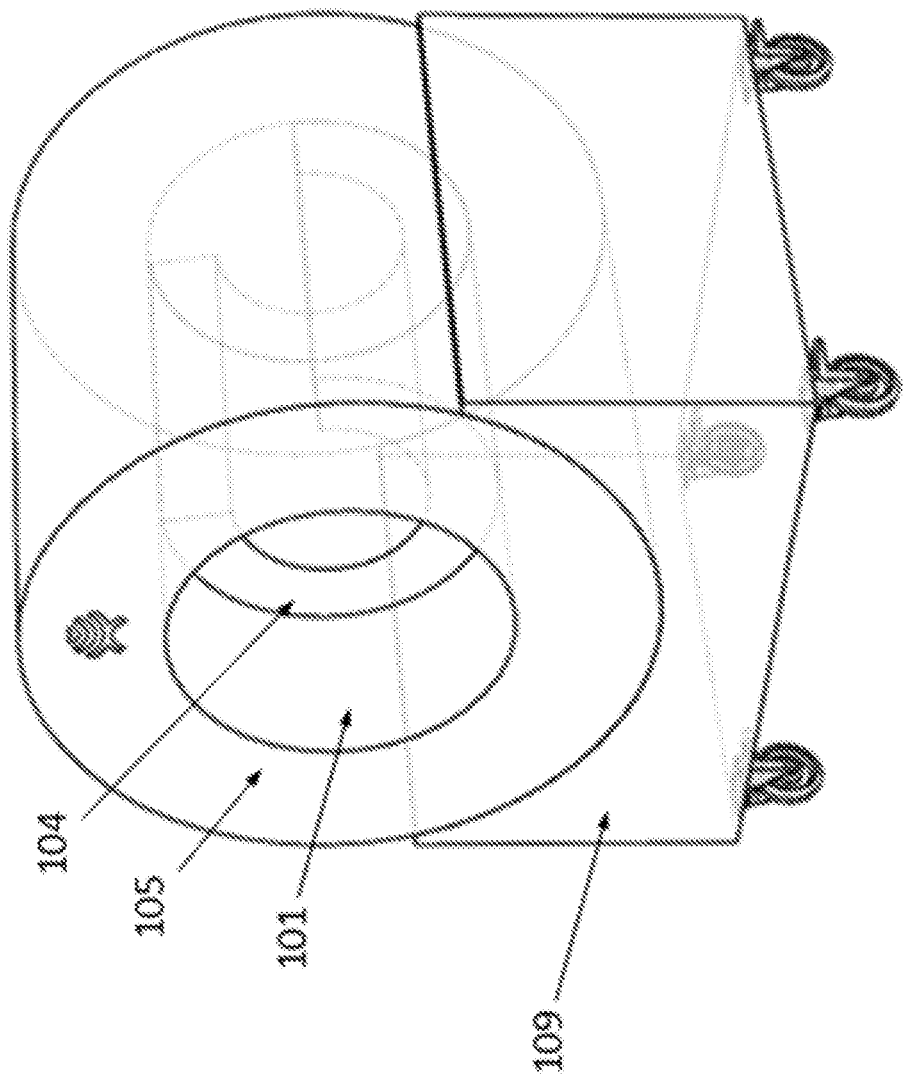
FIG. 1 shows a perspective view of an example of a magnetic resonance imaging (MRI) system.

Referring now to FIG. 1, an example of a magnetic resonance imaging (MRI) system 100 is shown in which a magnet housing 105 is placed on a base 109. Base 109 may include a portable cart, as shown. In some installations, base 109 may be affixed to the floor of the scanning room. Magnet housing 105 includes a solenoid magnet and bore area 101, where a human patient may be placed to be scanned. The solenoid magnet may be generally known as the main magnet. The solenoid magnet may generate a substantially uniform magnetic field for imaging the human patient placed inside bore area 101. This magnetic field may generally serve as a static polarizing field.

Figure 2:
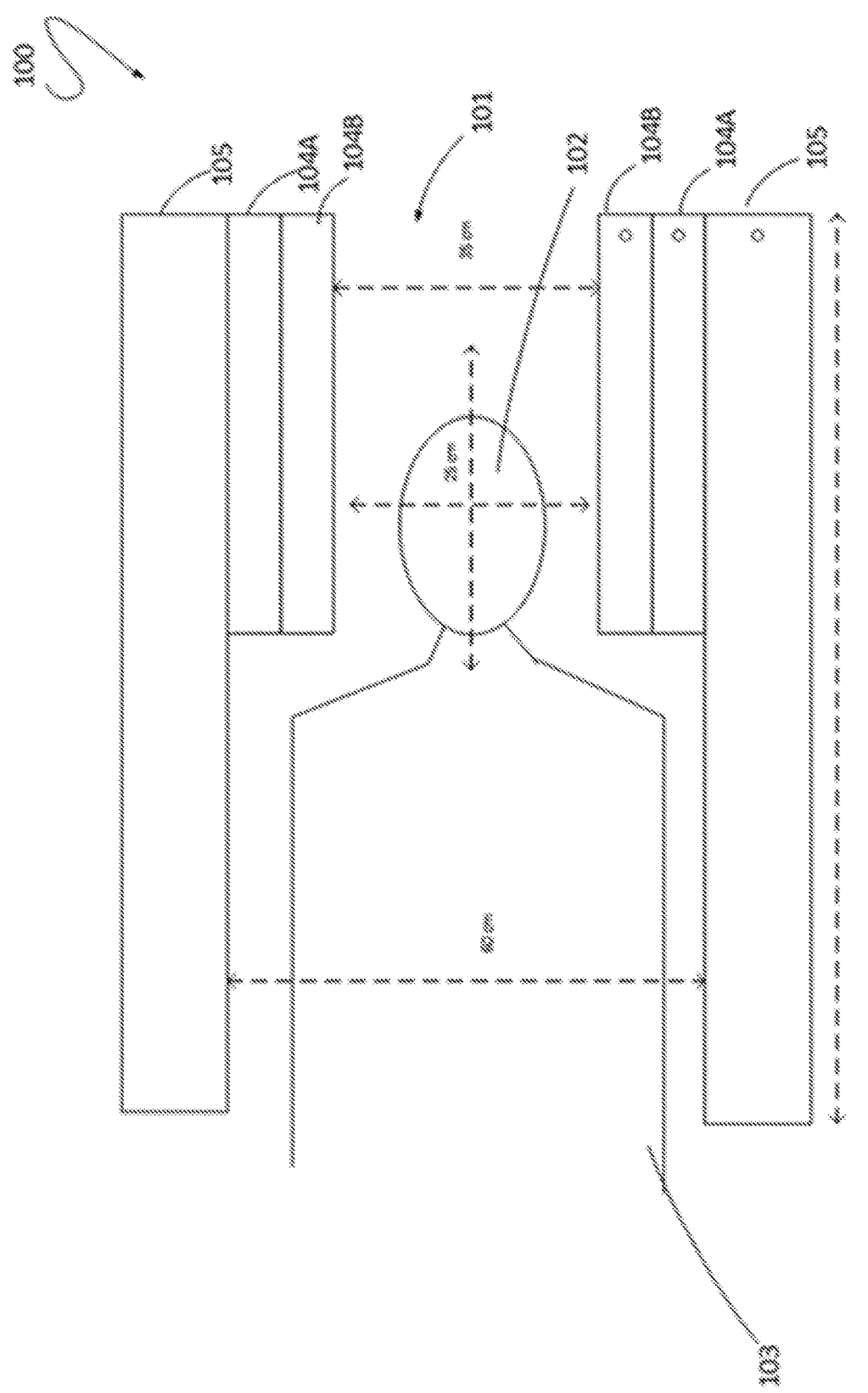
FIG. 2 shows a profile view of the MRI system.

Referring to FIG. 2, patient 103 may be placed in bore area 101. In this example, patient head area 102 is placed inside the magnetic field to be imaged by coil assembly 104. As shown in FIGS. 1 and 2, coil assembly 104 is shaped as an annular structure and housed within the inner bore of solenoid magnet. In this example, coil assembly 104 includes a gradient coil 104A and an RF coil 104B. The gradient coil 104A may generate a perturbation of the static polarizing field to encode magnetizations within the human patient's body. In some configurations, coil assembly 104 may include a radio frequency (RF) coil 104B to transmit RF pulses as excitation pulses. The RF coil 104B may also be configured to receive MR signals from the human patient in response to the RF pulses. In some instances, housing 105 may include separate receive coils to receive the MR signals from the human patient. In these instances, radio-frequency (RF) signals are, for example, transmitted by local coils for imaging a subject. In one example, a head coil in a birdcage configuration is used for both transmitting and receiving RF signals for imaging the subject's head area 102. In another instance, a surface coil is used for transmitting an RF signal into the subject and a phased array coil configuration is used for receiving MR signals in response.

Figure 3:
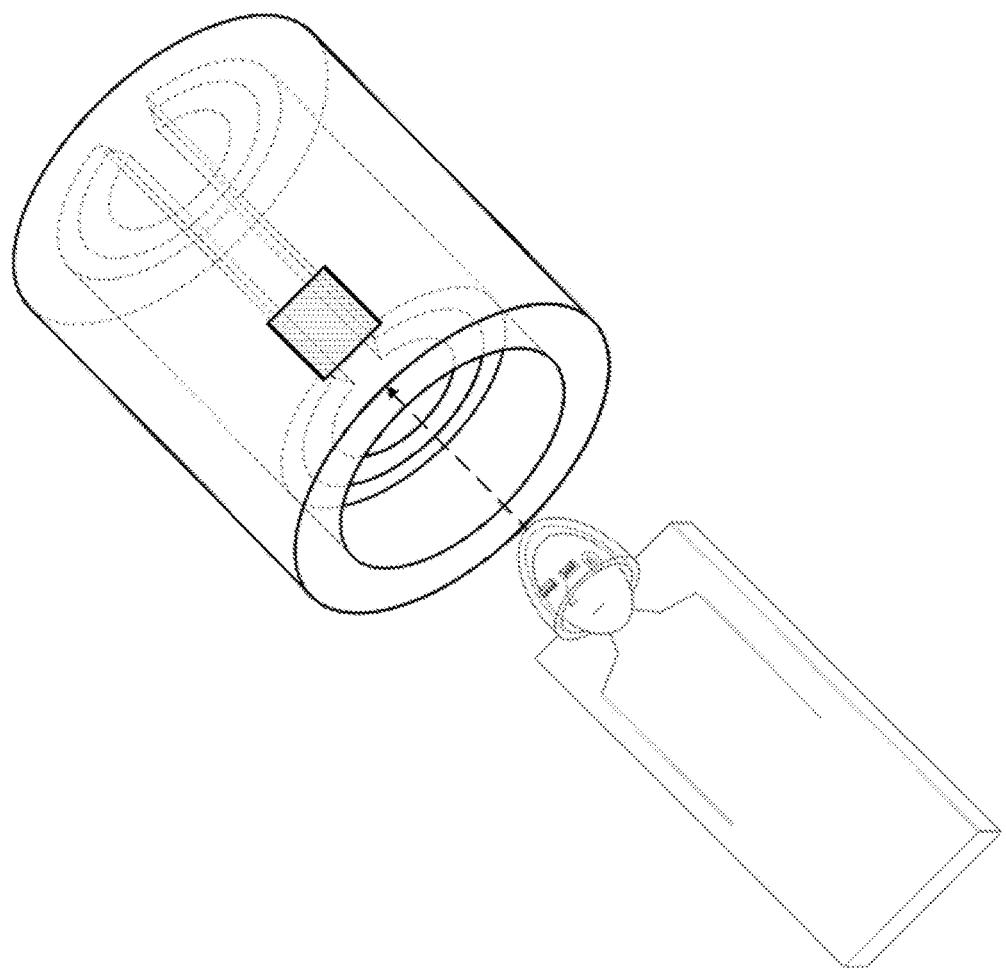
FIG. 3 shows an example embodiment illustrating the insertion of patient, wearing a head coil, into a magnetic resonance imaging system having a coil assembly with an aperture formed therein.

FIG. 3 shows an example embodiment illustrating the insertion of patient 160, supported by a table or stretcher 180, and wearing a head coil 230, into a magnetic resonance imaging system having a coil assembly with an aperture formed therein. In one instance, head coil 230 may be configured as a radio-frequency receiver coil as a local coil. In this instance, head coil 230 is configured to receive radio-frequency signals emitted from within the subject's head and in response to excitation radio frequency pulses sent from the transmit coil 130 within the annular coil assembly 135. In another instance, head coil 230 may be configured as a radio-frequency transmit and receiver coil. In the example embodiment shown, the aperture includes a display device, screen and/or camera 252. The coil assembly and associated aperture may be rotatable to accommodate multiple patient orientations. The system includes an initial gap region 240 configured to accommodate the patient's shoulders and torso. The receiving coil may be positioned about the patient with the aperture as desired prior to installing them within the magnet. In this embodiment, the rotating coil assembly 135 includes the gradient coil 120 and transmitting coil 130.

Figure 4:
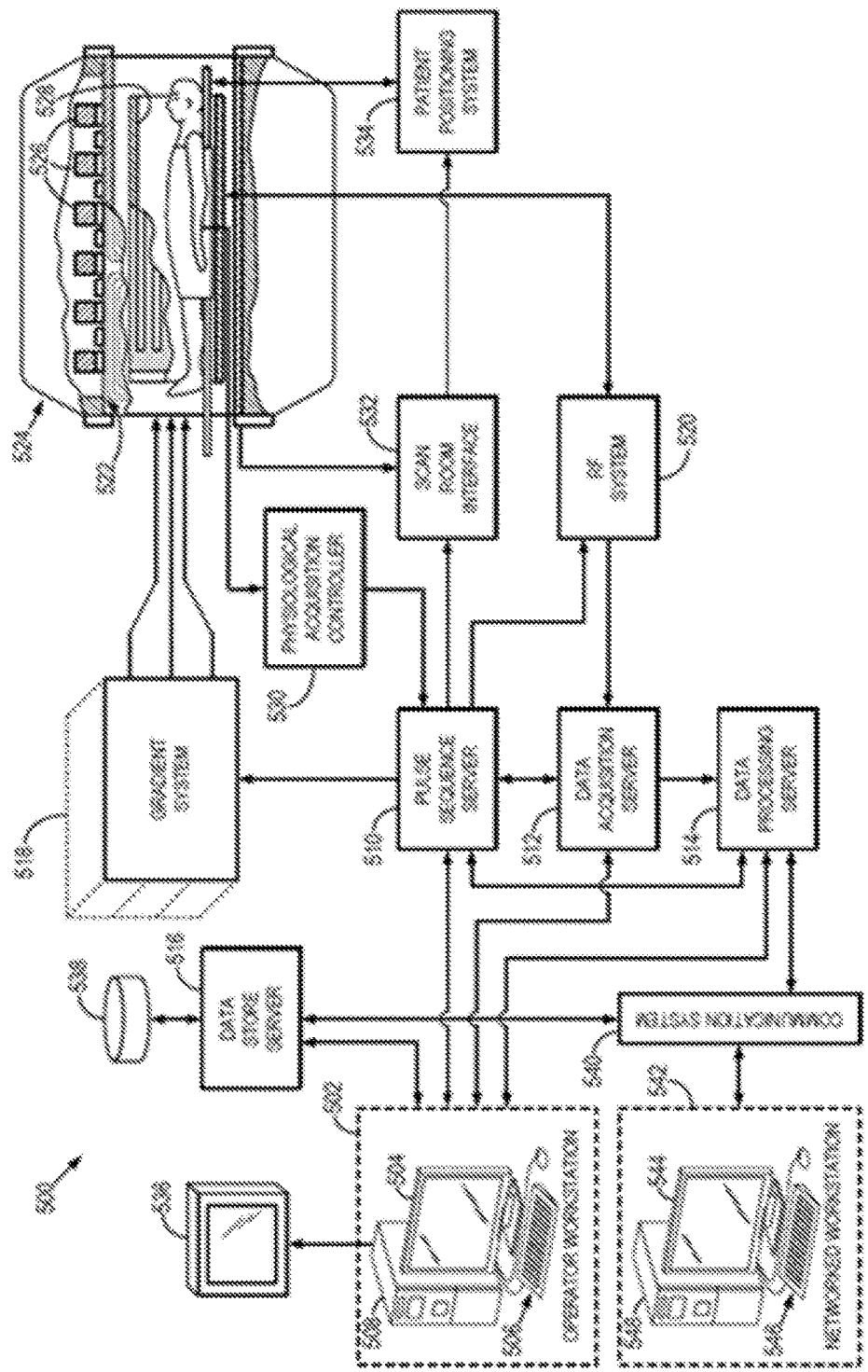
FIG. 4 is a block diagram of an example of an MRI system.

Referring particularly now to FIG. 4, an example of a magnetic resonance imaging ("MRI") system 500 is illustrated. The MRI system 500 includes an operator workstation 502, which will typically include a display 504; one or more input devices 506, such as a keyboard and mouse; and a processor 508. The processor 508 may include a commercially available programmable machine running a commercially available operating system. The operator workstation 502 provides the operator interface that enables scan prescriptions to be entered into the MRI system 500. In general, the operator workstation 502 may be coupled to four servers: a pulse sequence server 510; a data acquisition server 512; a data processing server 514; and a data store server 516. The operator workstation 502 and each server 510, 512, 514, and 516 are connected to communicate with each other. For example, the servers 510, 512, 514, and 516 may be connected via a communication system 540, which may include any suitable network connection, whether wired, wireless, or a combination of both. As an example, the communication system 540 may include both proprietary or dedicated networks, as well as open networks, such as the internet.

The pulse sequence server 510 functions in response to instructions downloaded from the operator workstation 502 to operate a gradient system 518 and a radiofrequency ("RF") system 520. Gradient waveforms necessary to perform the prescribed scan are produced and applied to the gradient system 518, which excites gradient coils in an assembly 522 to produce the magnetic field gradients $G_x$, $G_y$, and $G_z$ used for position encoding magnetic resonance signals. The gradient coil assembly 522 forms part of a magnet assembly 524 that includes a polarizing magnet 526 and a whole-body RF coil 528.

RF waveforms are applied by the RF system 520 to the RF coil 528, or a separate local coil (not shown in FIG. 4), in order to perform the prescribed magnetic resonance pulse sequence. Responsive magnetic resonance signals detected by the RF coil 528, or a separate local coil (not shown in FIG. 4), are received by the RF system 520, where they are amplified, demodulated, filtered, and digitized under direction of commands produced by the pulse sequence server 510. The RF system 520 includes an RF transmitter for producing a wide variety of RF pulses used in MRI pulse sequences. The RF transmitter is responsive to the scan prescription and direction from the pulse sequence server 510 to produce RF pulses of the desired frequency, phase, and pulse amplitude waveform. The generated RF pulses may be applied to the whole-body RF coil 528 or to one or more local coils or coil arrays (not shown in FIG. 4).

The RF system 520 also includes one or more RF receiver channels. Each RF receiver channel includes an RF preamplifier that amplifies the magnetic resonance signal received by the coil 528 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \qquad (1)$$

and the phase of the received magnetic resonance signal may also be determined according to the following relationship:

$$\varphi = \tan^{-1}\left(\frac{Q}{I}\right). \qquad (2)$$

The pulse sequence server 510 also optionally receives patient data from a physiological acquisition controller 530. By way of example, the physiological acquisition controller 530 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 510 to synchronize, or "gate," the performance of the scan with the subject's heart beat or respiration.

The pulse sequence server 510 also connects to a scan room interface circuit 532 that receives signals from various sensors associated with the condition of the patient and the magnet system. It is also through the scan room interface circuit 532 that a patient positioning system 534 receives commands to move the patient to desired positions during the scan.

The digitized magnetic resonance signal samples produced by the RF system 520 are received by the data acquisition server 512. The data acquisition server 512 operates in response to instructions downloaded from the operator workstation 502 to receive the real-time magnetic resonance data and provide buffer storage, such that no data is lost by data overrun. In some scans, the data acquisition server 512 does little more than pass the acquired magnetic resonance data to the data processor server 514. However, in scans that require information derived from acquired magnetic resonance data to control the further performance of the scan, the data acquisition server 512 is programmed to produce such information and convey it to the pulse sequence server 510. For example, during prescans, magnetic resonance data is acquired and used to calibrate the pulse sequence performed by the pulse sequence server 510. As another example, navigator signals may be acquired and used to adjust the operating parameters of the RF system 520 or the gradient system 518, or to control the view order in which k-space is sampled. In still another example, the data acquisition server 512 may also be employed to process magnetic resonance signals used to detect the arrival of a contrast agent in a magnetic resonance angiography ("MRA") scan. By way of example, the data acquisition server 512 acquires magnetic resonance data and processes it in real-time to produce information that is used to control the scan.

The data processing server 514 receives magnetic resonance data from the data acquisition server 512 and processes it in accordance with instructions downloaded from the operator workstation 502. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 514 are conveyed back to the operator workstation 502 where they are stored. Real-time images are stored in a data base memory cache (not shown in FIG. 4), from which they may be output to operator display 504 or a display 536 that is located near the magnet assembly 524 for use by attending physicians. Batch mode images or selected real time images are stored in a host database on disc storage 538. When such images have been reconstructed and transferred to storage, the data processing server 514 notifies the data store server 516 on the operator workstation 502. The operator workstation 502 may be used by an operator to archive the images, produce films, or send the images via a network to other facilities.

The MRI system 500 may also include one or more networked workstations 542. By way of example, a networked workstation 542 may include a display 544; one or more input devices 546, such as a keyboard and mouse; and a processor 548. The networked workstation 542 may be located within the same facility as the operator workstation 502, or in a different facility, such as a different healthcare institution or clinic.

The networked workstation 542, whether within the same facility or in a different facility as the operator workstation 502, may gain remote access to the data processing server 514 or data store server 516 via the communication system 540. Accordingly, multiple networked workstations 542 may have access to the data processing server 514 and the data store server 516. In this manner, magnetic resonance data, reconstructed images, or other data may be exchanged between the data processing server 514 or the data store server 516 and the networked workstations 542, such that the data or images may be remotely processed by a networked workstation 542. This data may be exchanged in any suitable format, such as in accordance with the transmission control protocol ("TCP"), the internet protocol ("IP"), or other known or suitable protocols.

Figure 5:
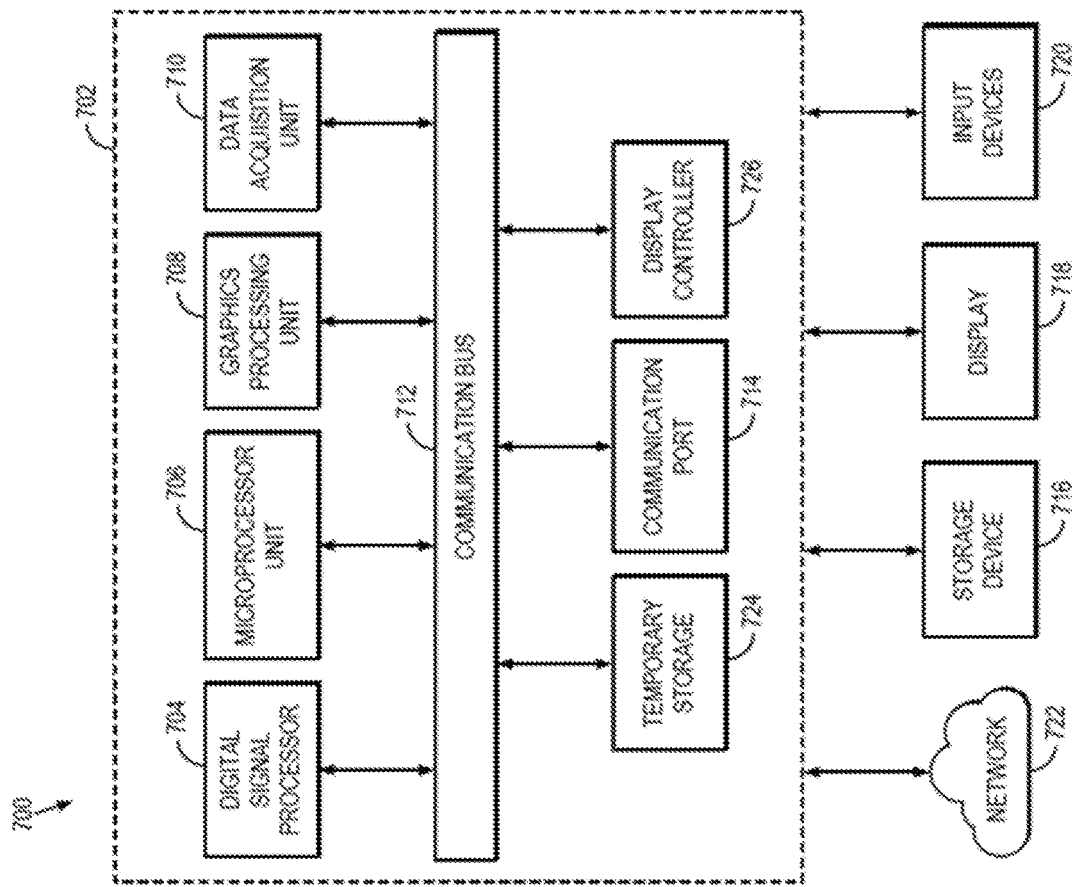
FIG. 5 is a block diagram of an example computer system that may be configured to implement the methods described herein.

Referring now to FIG. 5, a block diagram of an example computer system 700 that may be configured to co-register medical images acquired with different imaging modalities, as described above, is illustrated. The medical images to be co-registered may be provided to the computer system 700 from the respective medical imaging systems, such as an MRI system and a CT system, or from a data storage device, and are received in a processing unit 702.

In some embodiments, the processing unit 702 may include one or more processors. As an example, the processing unit 702 may include one or more of a digital signal processor ("DSP") 704, a microprocessor unit ("MPU") 706, and a graphics processing unit ("GPU") 708. The processing unit 702 may also include a data acquisition unit 710 that is configured to electronically receive data to be processed, which may include first and second medical images, image series, or image volumes. The DSP 704, MPU 706, GPU 708, and data acquisition unit 710 are all coupled to a communication bus 712. As an example, the communication bus 712 may be a group of wires, or a hardwire used for switching data between the peripherals or between any component in the processing unit 702.

The DSP 704 may be configured to receive and processes the first and second medical images. The MPU 706 and GPU 708 may also be configured to process the first and second medical images in conjunction with the DSP 704. As an example, the MPU 706 may be configured to control the operation of components in the processing unit 702 and may include instructions to perform processing of the first and second medical images on the DSP 704. Also as an example, the GPU 708 may process image graphics.

In some embodiments, the DSP 704 may be configured to process the first and second medical images received by the processing unit 702 in accordance with the algorithms described above. Thus, the DSP 704 may be configured to identify anatomical features in the images, to calculate registration parameters based on the identified anatomical features and known spatial relationships there between, and to co-register the images using the registration parameters.

The processing unit 702 preferably includes a communication port 714 in electronic communication with other devices, which may include a storage device 716, a display 718, and one or more input devices 720. Examples of an input device 720 include, but are not limited to, a keyboard, a mouse, and a touch screen through which a user may provide an input.

The storage device 716 is configured to store images, whether provided to or processed by the processing unit 702. The display 718 is used to display images, such as images that may be stored in the storage device 716, and other information. Thus, in some embodiments, the storage device 716 and the display 718 may be used for displaying the images before and after registration and for outputting other information, such as data plots or other reports based on the registration process.

The processing unit 702 may also be in electronic communication with a network 722 to transmit and receive data, including CT images, MR images, and other information. The communication port 714 may also be coupled to the processing unit 702 through a switched central resource, for example the communication bus 712.

The processing unit 702 may also include a temporary storage 724 and a display controller 726. As an example, the temporary storage 724 may store temporary information. For instance, the temporary storage 724 may be a random access memory.

Implementations relating to determining a scan orientation are next described which may be used within MRI devices and/or systems described heretofore, and/or within other medical imaging systems and/or devices.

Figure 6:
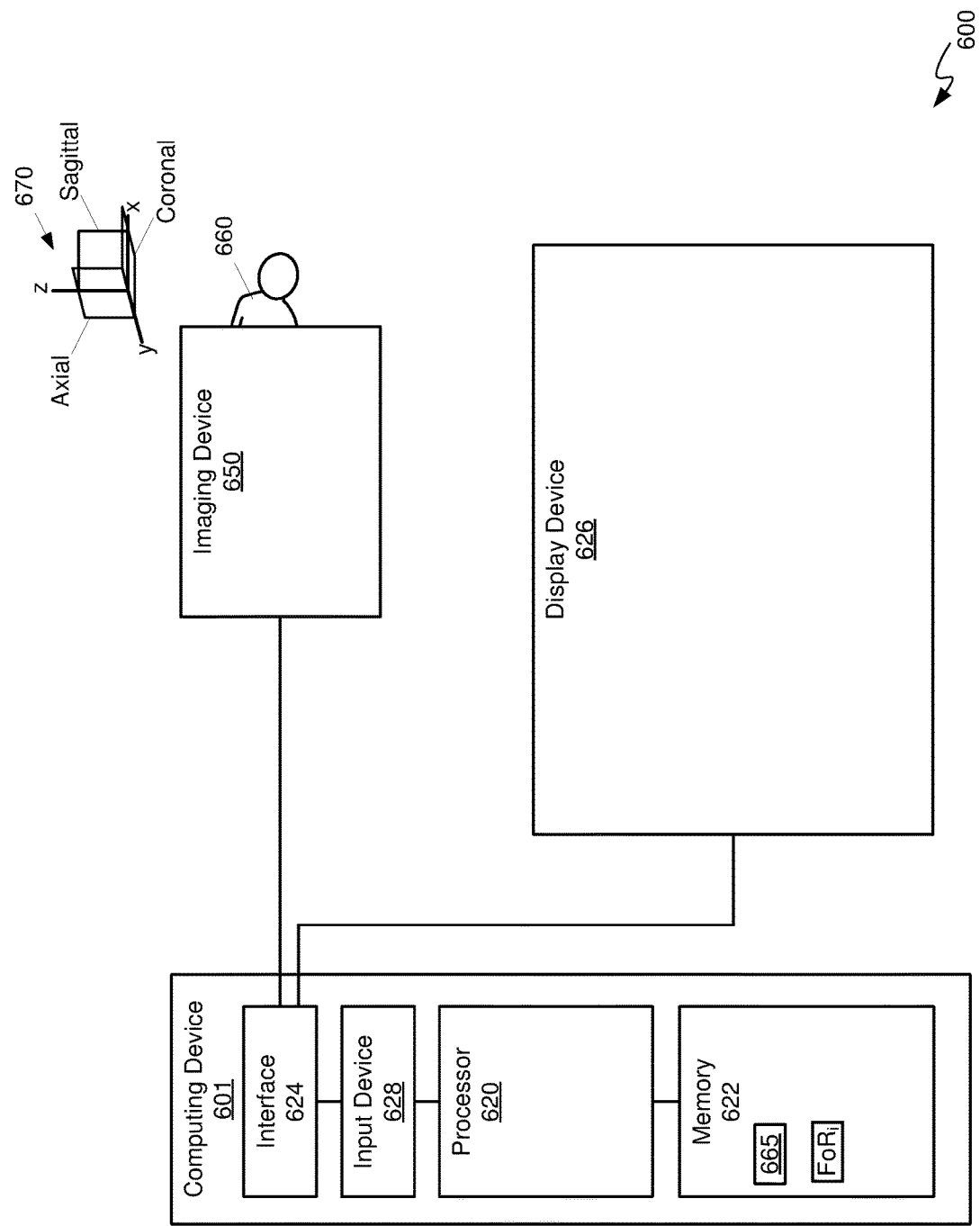
FIG. 6 depicts a medical imaging system for determining a scan orientation, according to non-limiting implementations.

Hence, attention is next directed to FIG. 6, which depicts a medical imaging system 600 for determining a scan orientation, medical imaging system 600 comprising: a computing device 601 comprising a processor 620, a memory 622, and a communication interface 624; a display device 626; an input device 628 configured to provide interactions with display device 626; and, an imaging device 650 configured to acquire digital images, computing device 601 configured to communicate with display device 626 and imaging device 650 using communication interface 624, processor 620 configured to: instruct imaging device 650 to acquire at least a sagittal scout scan, an axial scout scan and a coronal scout scan, based on an initial frame of reference, the initial frame of reference based on one or more of the imaging device 650 and a patient located in the imaging device 650; render, at the display device 626: a two-dimensional representation of each of the sagittal scout scan, the axial scout scan and the coronal scout scan; render, at the display device 626, initial respective selections of a portion of each of the sagittal scout scan, the axial scout scan and the coronal scout scan, oriented according to the initial frame of reference, the initial respective selections representing an initial field of view of an acquisition volume of imaging device 650, the initial respective selections being automatically selected according to the initial frame of reference; receive, from the input device 628, input indicating a respective reorientation of one or more of the initial respective selections; transform the initial frame of reference using the respective reorientation of one or more of the initial respective selections to produce a reoriented frame of reference; and, instruct the imaging device 650 to acquire further images based on the reoriented frame of reference.

Computing device 601 may comprise one or more of operator workstation 502, networked workstation 542, depicted in FIG. 4, and computer system 700, depicted in FIG. 5, with processor 620, memory 622 and communication interface 624 corresponding to suitable components of operator workstation 502, networked workstation 542, and/or computer system 700; hence, while not depicted, computing device 601 may also comprise other components such as one or more input devices. Display device 626 may comprise a display device of one or more of operator workstation 502, networked workstation 542, and/or computer system 700, and may be integrated with computing device 601 and/or comprise a stand-alone display device, such as a monitor and the like. In particular, display device 626 may comprise any suitable one of or combination of CRT (cathode ray tube) and/or flat panel displays (e.g. LCD (liquid crystal display), plasma, OLED (organic light emitting diode), capacitive or resistive touch screens, and the like. In some implementations, display device 626 comprises a touch screen, such that display device 626 comprises input device 628.

Indeed, input device 628 may comprise one or more of: a touchscreen at display device 628, a mouse, a rotatable mouse, a foot pedal, a microphone configured to receive voice commands, and a gesture-based input device. Other types of input devices will occur to persons of skill in the art and are within the scope of present implementations.

While MRI devices have been described in detail heretofore, other types of imaging devices that acquire scout scans and/or images as described herein are within the scope of present implementations. As such, imaging device 650 may comprise one or more of: a magnetic resonance imaging (MRI) device, an Optical Coherence Tomography (OCT) device, a computerized tomography (CT) device a computerized axial tomography (CAT) device, and a positron emission tomography (PET) device. Regardless, imaging device 650 is generally configured to acquire digital images of a sample, which may include, but is no limited to, a patient 660, as depicted.

Furthermore, while a head and shoulders of patient 660 is depicted as being external to imaging device 650, this depiction is for clarity only and it is assumed that the head and shoulders of patient 660 may be within imaging device 650 such that the head and shoulders of patient 660 may be scanned using imaging device 650.

Processor 620 may be implemented as a plurality of processors, including but not limited to one or more central processors (CPUs) and/or one or more processing units; either way, processor 620 comprises a hardware element and/or a hardware processor of computing device 601. Processor 620 is configured to communicate with memory 622 comprising a non-volatile storage unit (e.g. Erasable Electronic Programmable Read Only Memory ("EEPROM"), Flash Memory) and a volatile storage unit (e.g. random access memory ("RAM")). Furthermore, when processor 620 is implemented as a plurality of processors, at least a first processor may be configured to communicate with imaging device 650 using interface 624, and at least a second processor may be configured to communicate with display device 626; the various processors may be in communication with each other. Programming instructions that implement the functional teachings of computing device 601 as described herein are typically maintained, persistently, in memory 622 and used by processor 620 which makes appropriate utilization of volatile storage during the execution of such programming instructions. Those skilled in the art recognize that memory 622 is an example of computer readable media that may store programming instructions executable on processor 620. Furthermore, memory 622 is also an example of a memory unit and/or memory module and/or a non-volatile memory and/or a non-transitory computer readable medium.

In particular, memory 622 stores an application 665 comprising a computer program, wherein execution of the computer program, for example by processor 620, is for: instruct imaging device 650 to acquire at least a sagittal scout scan, an axial scout scan and a coronal scout scan, based on an initial frame of reference, the initial frame of reference based on one or more of imaging device 650 and a patient located in the imaging device 650; render, at the display device 626: a two-dimensional representation of each of the sagittal scout scan, the axial scout scan and the coronal scout scan; render, at the display device 626, initial respective selections of a portion of each of the sagittal scout scan, the axial scout scan and the coronal scout scan, oriented according to the initial frame of reference, the initial respective selections representing an initial field of view of an acquisition volume of imaging device 650, the initial respective selections being automatically selected according to the initial frame of reference; receive, from the input device 628, input indicating a respective reorientation of one or more of the initial respective selections; transform the initial frame of reference using the respective reorientation of one or more of the initial respective selections to produce a reoriented frame of reference; and, instruct the imaging device 650 to acquire further images based on the reoriented frame of reference.

Furthermore, imaging device 650 is associated with a frame of reference (FOR) 670 comprising an axial plane, a sagittal plane and a coronal plane, and/or a first axis (e.g. as depicted, the "x" axis), a second axis (e.g. as depicted, the "y" axis), and a third axis (e.g. as depicted, the "z" axis). As depicted, each of the planes and/or axes of FOR 670 is aligned with a longitudinal axis of imaging device 650 and/or is perpendicular to the longitudinal axis of imaging device 650. Data representative of FOR 670 may be stored at memory 622 as $FOR_i$.

System 600 may initially be configured to acquire digital images of patient 600 with the scanning oriented along FOR 670. Hence, FOR 670 may comprise an initial frame of reference. For example, when imaging device 650 comprises an MRI device, magnetic gradients are oriented with respect to FOR 670; in other words, such magnetic gradients may be in a direction of the axial plane, the sagittal plane and the coronal plane and/or any of the first axis, the second axis and the third axis.

However, patient 660 need not be aligned with FOR 670. Indeed, as depicted, patient 660 has been placed into a position where patient forms an angle with each of axes and/or planes of FOR 670. This creates a problem when scanning patient 660 using imaging device 650 as scanning of patient 660 may be more efficient when such scanning occurs according to, for example, a longitudinal axis of patient 660 and/or axes and/or planes of FOR 670. However, even when patient 660 is aligned with FOR 670, scanning of patient 660 along axes and/or planes other than axes and/or planes of FOR 670 may be preferred by a surgeon, for example along axes and/or planes commensurate with surgery that is to occur on patient 660.

For example, while not depicted, in some implementations, system 600 may further comprising a device configured to acquire a patient frame of reference of patient 660 located in imaging device 150, processor 620 in communication with the device configured to acquire a patient frame of reference; in these implementations, the initial frame of reference may be based on the patient frame of reference as determined from communications with the device configured to acquire a patient frame of reference. Still, the patient frame of reference may not be commensurate with surgery that is to occur on patient 660.

Figure 7:
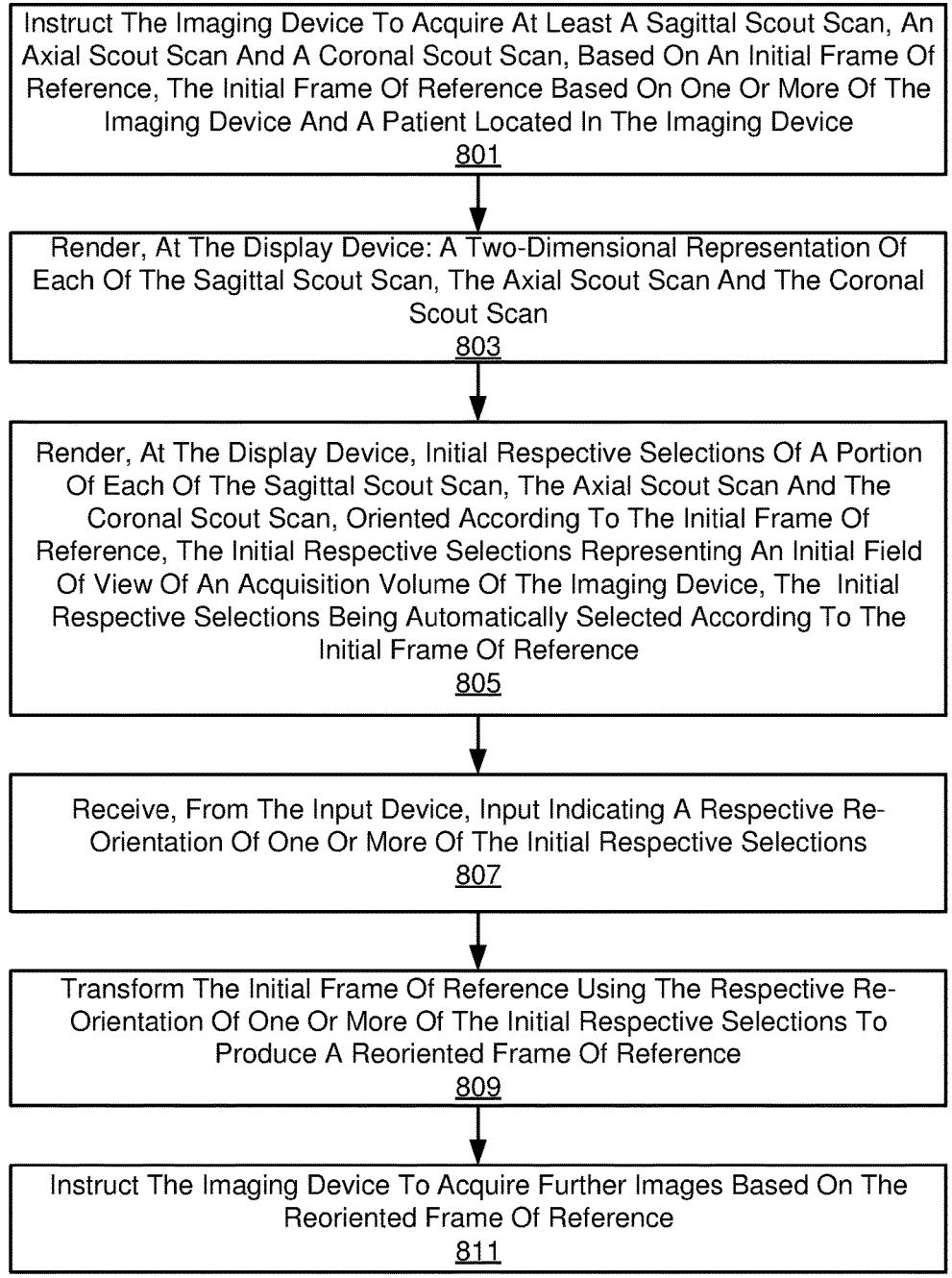
FIG. 7 depicts a method for determining a scan orientation in a medical imaging system, according to non-limiting implementations.

Hence, attention is now directed to FIG. 7 which depicts a flowchart of a method 800 for determining a scan orientation in a medical imaging system, according to non-limiting implementations. In order to assist in the explanation of method 800, it will be assumed that method 800 is performed using system 600, and specifically by processor 620 of computing device 601, for example when processor 620 processes application 665. Indeed, method 800 is one way in which computing device 101 may be configured. Furthermore, the following discussion of method 800 will lead to a further understanding of computing device 601, and system 600 and its various components. However, it is to be understood that system 600 and/or method 800 may be varied, and need not work exactly as discussed herein in conjunction with each other, and that such variations are within the scope of present implementations.

Regardless, it is to be emphasized, that method 800 need not be performed in the exact sequence as shown, unless otherwise indicated; and likewise various blocks may be performed in parallel rather than in sequence; hence the elements of method 800 are referred to herein as "blocks" rather than "steps". It is also to be understood, however, that method 800 may be implemented on variations of system 600 as well.

At block 801, processor 620 instructs imaging device 650 to acquire at least a sagittal scout scan, an axial scout scan and a coronal scout scan, based on an initial frame of reference, the initial frame of reference based on one or more of the imaging device 650 and a patient located in the imaging device 650.

At block 803, processor 620 renders, at the display device 626: a two-dimensional representation of each of the sagittal scout scan, the axial scout scan and the coronal scout scan.

At block 805, processor 620 renders, at the display device 626, initial respective selections of a portion of each of the sagittal scout scan, the axial scout scan and the coronal scout scan, oriented according to the initial frame of reference, the initial respective selections representing an initial field of view of an acquisition volume of imaging device 650, the initial respective selections being automatically selected according to the initial frame of reference.

At block 807, processor 620 receives, from the input device 628, input indicating a respective reorientation of one or more of the initial respective selections.

At block 809, processor 620 transforms the initial frame of reference using the respective reorientation of one or more of the respective initial respective selections to produce a reoriented frame of reference.

At block 811, processor 620 instructs the imaging device 650 to acquire further images based on the reoriented frame of reference.

Method 800 will now be discussed with reference to: FIGS. 8 to 11, each of which are substantially similar to each other, with like elements having like numbers; FIG. 12, which is substantially similar to FIG. 6, with like elements having like numbers; and FIGS. 13 to 17, each of which are substantially similar to each other, with like elements having like numbers.

Figure 8:
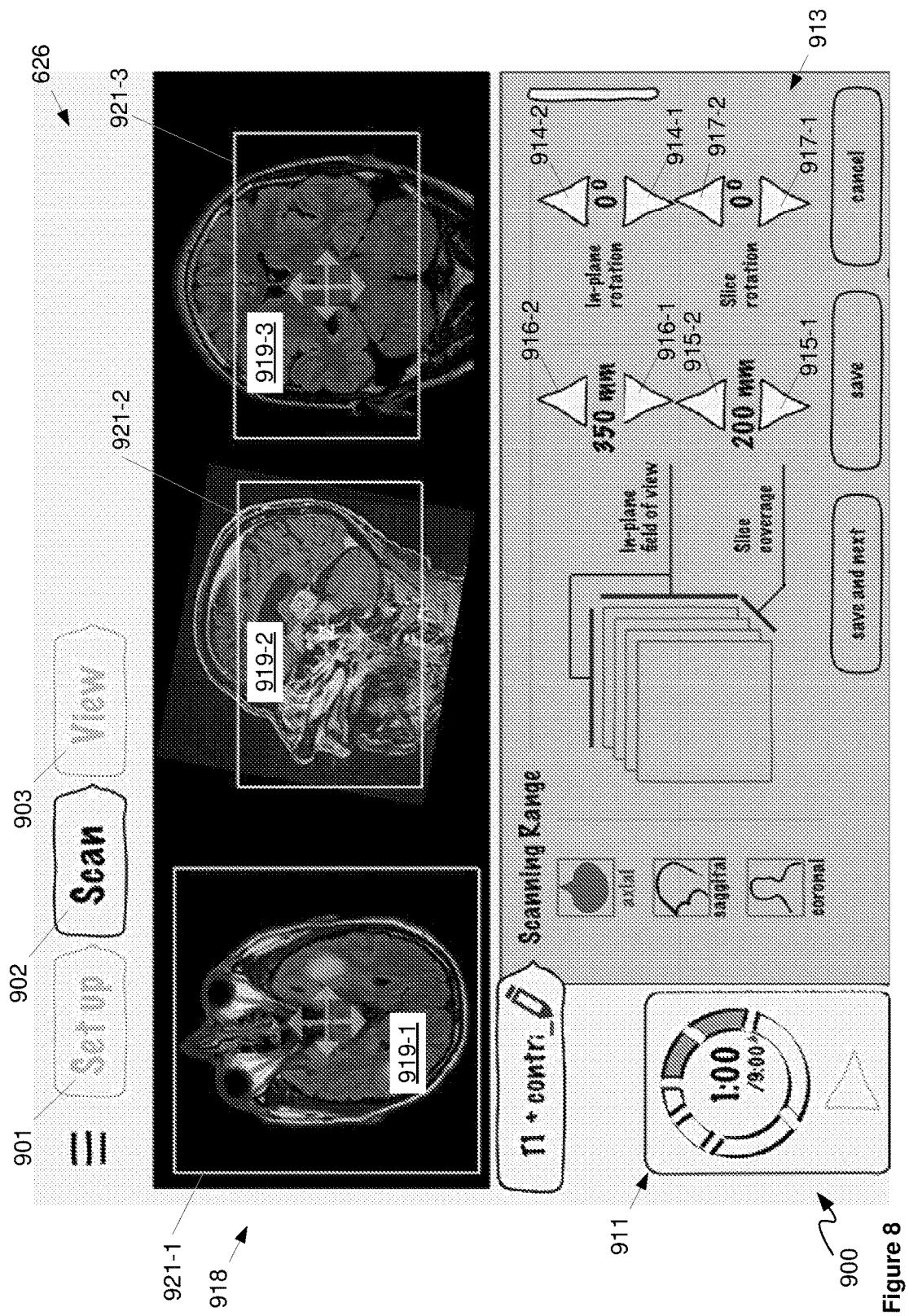
FIG. 8 depicts a GUI for determining a scan orientation in the medical imaging system of FIG. 6, according to non-limiting implementations.

For example, attention is next directed to FIG. 8, which depicts display device 626 rendering a graphic user interface (GUI) 900 under control of processor 620, for example when processor 620 is processing application 665, and processor 620 is implementing method 800. It is assumed in FIG. 8 that display device 626 comprises a touchscreen such that touch input may be received at display device 626 to control operation of computing device 601 and/or imaging device 650.

GUI 900 comprises: selectable options 901, 902, 903 which, when selected, causes processor 620 to control one or more of computing device 601 and imaging device 650 to operate in one or more modes, the one or more modes including one or more of: a setup mode wherein a scan prescription is generated; a scan mode wherein a plurality of digital image series is acquired; and a view mode wherein the plurality of digital image series are rendered at display device 626. However, selectable options 901, 902, 903 are appreciated to be optional, and other implementations of GUI 900 does not comprise such selectable options.

Selectable option 901, when selected (and when present), causes processor 620 to control at least computing device 601 to enter a setup mode (hence the label "Setup" on selectable option 901), wherein a scan is setup up and/or a scan prescription is generated. Similarly, selectable option 902, when selected (and when present), causes processor 620 to control at least computing device 601 and imaging device 650 to enter a scan mode (hence the label "Scan" on selectable option 901), wherein a digital images are acquired. And, selectable option 903, when selected (and when present), causes processor 620 to control at least computing device 601 to enter a view mode (hence the label "View" on selectable option 901), wherein the digital images are rendered at display device 626. Hence, each of selectable options 901, 902, 903 may comprise virtual buttons and the like, however other processes and/or methods for mode selection are within the scope of present implementations, including, but not limited to selecting a mode using pull-down menus and the like. Hence, selectable options 901, 902, 903, as depicted in FIG. 8, may be optional.

As depicted, selectable option 902 is selected as indicated by lines selectable option 902 being of a heavier weight than respective lines of selectable option 901, 903.

As further depicted in FIG. 8, processor 620 is further configured to render an area 913 comprising controls 914-1, 914-2, 915-1, 915-2, 916-1, 916-2, 917-1, 917-2 for controlling various scanning parameters including, but not limited to, increasing and decreasing in-plane rotation of a scan (respectively, controls 914-1, 914-2), increasing and decreasing slice coverage of a scan (respectively, controls 915-1, 916-2), increasing and decreasing in-plane field of view of a scan (respectively, controls 916-1, 916-2), and increasing and decreasing slice rotation of a scan (respectively, controls 917-1, 917-2). Controls 914-1, 914-2, 915-1, 915-2, 916-1, 916-2, 917-1, 917-2 will hereafter collectively be referred to as controls 914, 915, 916, 917 and generically as a control 914 and/or a control 915 and/or a control 916 and/or a control 917. In general, input device 629, for example a touchscreen of display device 626, may be used to interact with each control 914, 915, 916, 917. Other controls are present in GUI 900, but are not numbered, for example controls for saving, cancelling, selecting a scan to change with controls 914, 915, 916, 917 etc.

As further depicted in FIG. 8, processor 620 is further configured to render an area 918 comprising images acquired by image device 650 and/or other data as described in more detail below.

In other words, it is assumed in FIG. 8 that blocks 801, 803 of method 800 have been implemented at computing device 601, by processor 620.

It is further assumed in FIG. 8 that processor 620 has instructed imaging device 620 to acquire at least a sagittal scout scan, an axial scout scan and a coronal scout scan, based on an initial frame of reference, the initial frame of reference based on one or more of the imaging device and a patient located in imaging device 650, for example, patient 660. It is further assumed that imaging device 650 has acquired at least a sagittal scout scan, an axial scout scan and a coronal scout scan and transmitted respective images that include at least a sagittal scout scan, an axial scout scan and a coronal scout scan to computing device 601. For example, the initial frame of reference may comprise FOR 670, and each of the sagittal scout scan, the axial scout scan and the coronal scout scan acquired in conjunction with block 301, 303 occurs at least along the axial plane, the sagittal plane and the coronal plane of FOR 670.

In some implementations of block 801, 803, processor 620 is configured instruct imaging device 650 to acquire at least the sagittal scout scan, the axial scout scan and the coronal scout scan by instructing imaging device 650 to acquire a two-dimensional sagittal scout scan, a two-dimensional axial scout scan and a two-dimensional coronal scout scan. Specifically, in these implementations, computing device 610 instructs imaging device 650 to specifically acquire scans along the axial plane, the sagittal plane and the coronal plane of FOR 670 adjusting magnetic fields of imaging device 650 accordingly. Hence, in these implementations, a three-dimensional scout scan does not occur at imaging device 650.

Alternatively, processor 620 may be further configured to instruct imaging device 650 to acquire at least the sagittal scout scan, the axial scout scan and the coronal scout scan by instructing the imaging device to acquire a three-dimensional scout scan based on the initial frame reference, for example FOR 670. In these implementations, processor 620 instructs imaging device 650 to acquire a three-dimensional scout scan. In some of these implementations, instructions to acquire three-dimensional scout scan may include specific instructions to acquire the sagittal scout scan, the axial scout scan and the coronal scout scan; alternatively, acquisition of the three-dimensional scout scan may include acquisition of scans along the sagittal plane, the axial plane and the coronal plane by virtue of the magnetic field(s) being aligned therewith, but without specific instructions to acquire the sagittal scout scan, the axial scout scan and the coronal scout scan. In other words, the sagittal scout scan, the axial scout scan and the coronal scout scan may be extracted from the three-dimensional scout scan by processor 620 processing the three-dimensional scout scan. In other words, processor 620 may be further configured to extract the two-dimensional representation of each of the sagittal scout scan, the axial scout scan and the coronal scout scan from the three-dimensional scout scan, regardless of whether specific instructions to acquire the sagittal scout scan, the axial scout scan and the coronal scout scan are included or not.

In any event, as also depicted in FIG. 8, in area 918, adjacent area 913, processor 620 has rendered, at display device 626: a two-dimensional representation of each of the axial scout scan, the sagittal scout scan and the coronal scout scan, respectfully referred to hereafter as axial scout scan 919-1, sagittal scout scan 919-2, and coronal scout scan 919-3. Furthermore, it is appreciated that each of axial scout scan 919-1, sagittal scout scan 919-2, and coronal scout scan 919-3 comprise respective two-dimensional representations of each of the axial scout scan, the sagittal scout scan and the coronal scout scan performed by imaging device 650.

Furthermore, axial scout scan 919-1, sagittal scout scan 919-2, and coronal scout scan 919-3 will be interchangeably referred to hereafter, collectively, as scans 919 and, generically, as a scan 919. Hence, rendering of scans 919 assumes that processor 620 has implemented block 305 of method 300.

For example, assuming that MRI scans were performed on a head of patient 660, each of scans 919 represent a MRI scout scans of the head of patient 660. Hence, as will become clearer in the following description, GUI 900 generally conveys the relationship between the underlying anatomy and the surface of the anatomy of a patient to be further scanned using imaging device 650.

As also depicted in FIG. 8, in area 918, and in conjunction with each of scans 919, processor 620 has rendered, at display device 626, initial respective selections 921-1, 921-2, 921-3 of a portion of each of oriented according to initial frame of reference, e.g. FOR 670. Initial respective selections 921-1, 921-2, 921-3 will be interchangeably referred to hereafter, collectively, as selections 921 and, generically, as a selection 921.

As depicted, each of selections 921 comprises respective rectangles overlaid, at display device 626, on each of axial scout scan 919-1, sagittal scout scan 919-2, and coronal scout scan 919-3. In particular, each rectangle is automatically oriented according to initial FOR 670. In other words, each of axial scout scan 919-1, sagittal scout scan 919-2, and coronal scout scan 919-3 comprises a scan in a respective plane, and each of the respective rectangles are oriented in the respective plane.

In particular, the automatically selected initial respective selections (e.g. selections 921) of a portion of each of scans 919 may comprise at least one three-dimensional selection, for example of an acquisition volume to be scanned when obtaining further images, as described in more detail below. However, as in method 800, when selections 921 are reoriented, the frame of reference is transformed and/or reoriented, which may result in the three-dimensional selection and/or acquisition volume also being reoriented.

While each of controls 914, 915, 916, 917 may be used to change an orientation of each of selections 921, and the like, input device 628, such as a touchscreen, may be used to interact with selections 921 to reorient each selection 921.

Figure 9:
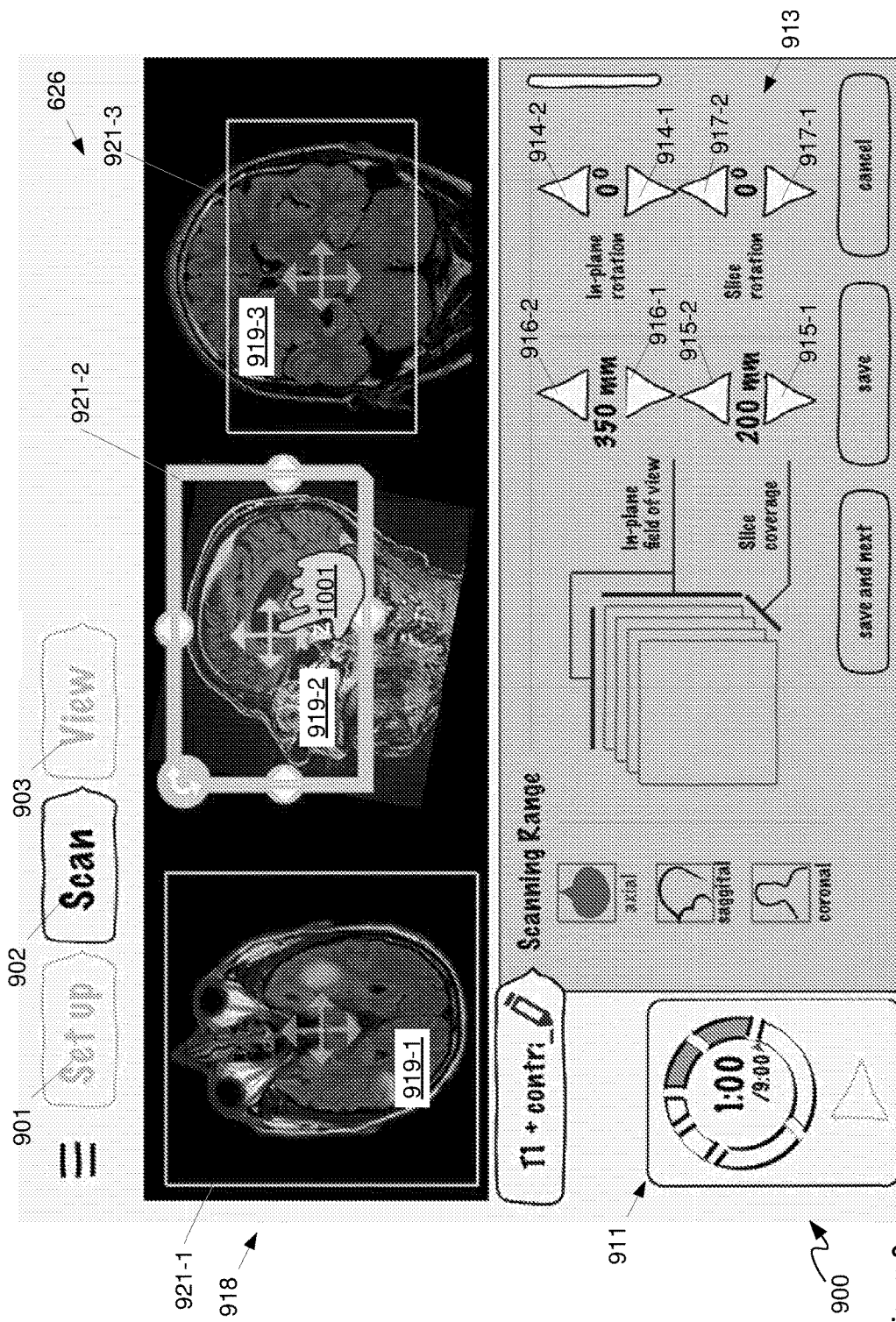
FIG. 9 depicts the GUI of FIG. 8 in which a representation of a selection of a scout scan is adjusted, according to non-limiting implementations.
Figure 10:
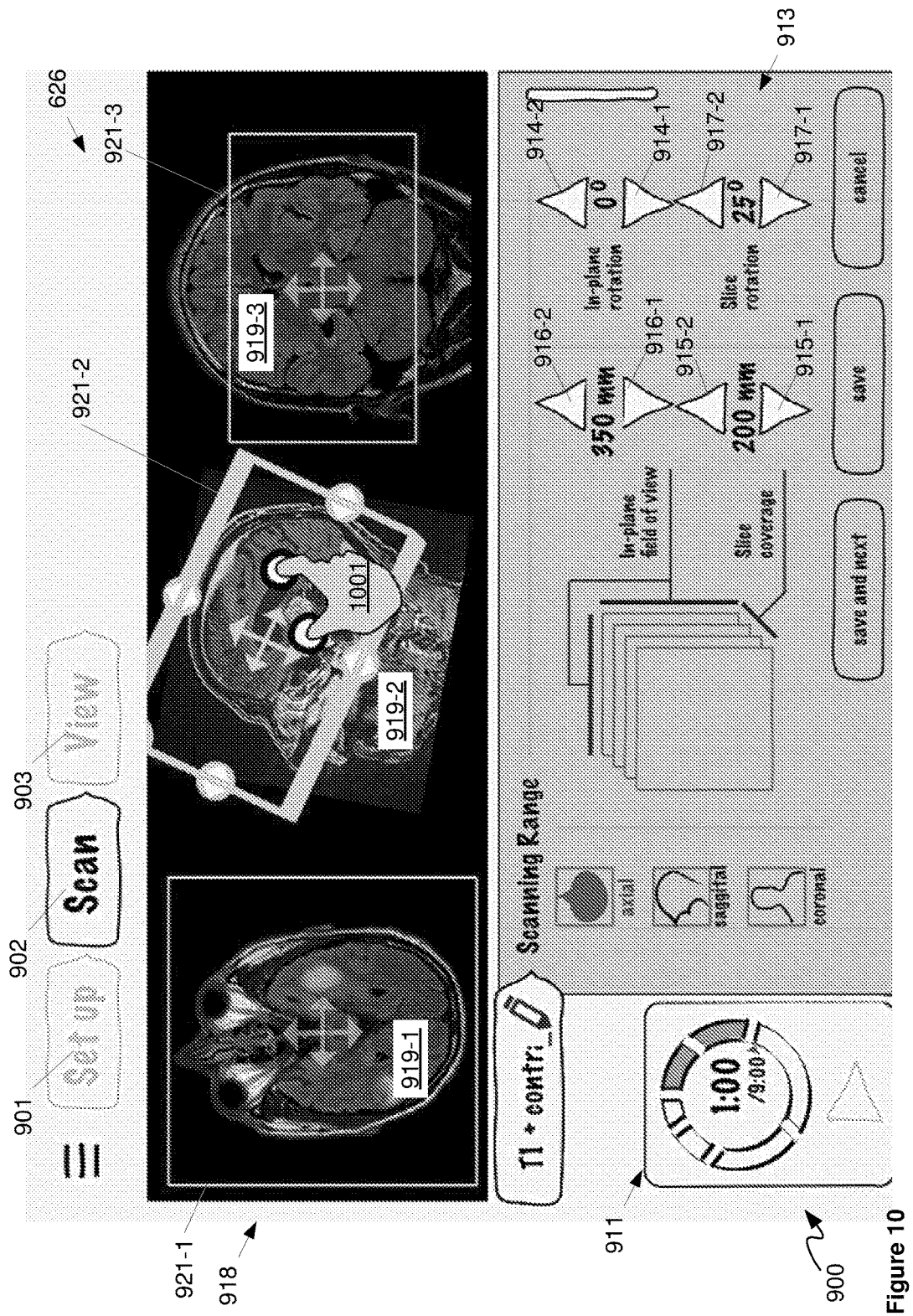
FIG. 10 depicts the GUI of FIG. 8 in which a representation of a selection of a scout scan is reoriented, according to non-limiting implementations.

For example, attention is directed to FIGS. 9 and 10, in which a hand 1001 of a user interacts with a touchscreen of display device 626 to reorient selection 921-2. In particular, in FIG. 9, selection 921-2 is moved "up" with respect to FIG. 8, and in FIG. 10, representation 921-2 is rotated; the degree of rotation is also reflected at controls 917 where the slice rotation, in FIG. 10, is 25° as compared to FIGS. 8 and 9, where the slice rotation is 0°.

Figure 11:
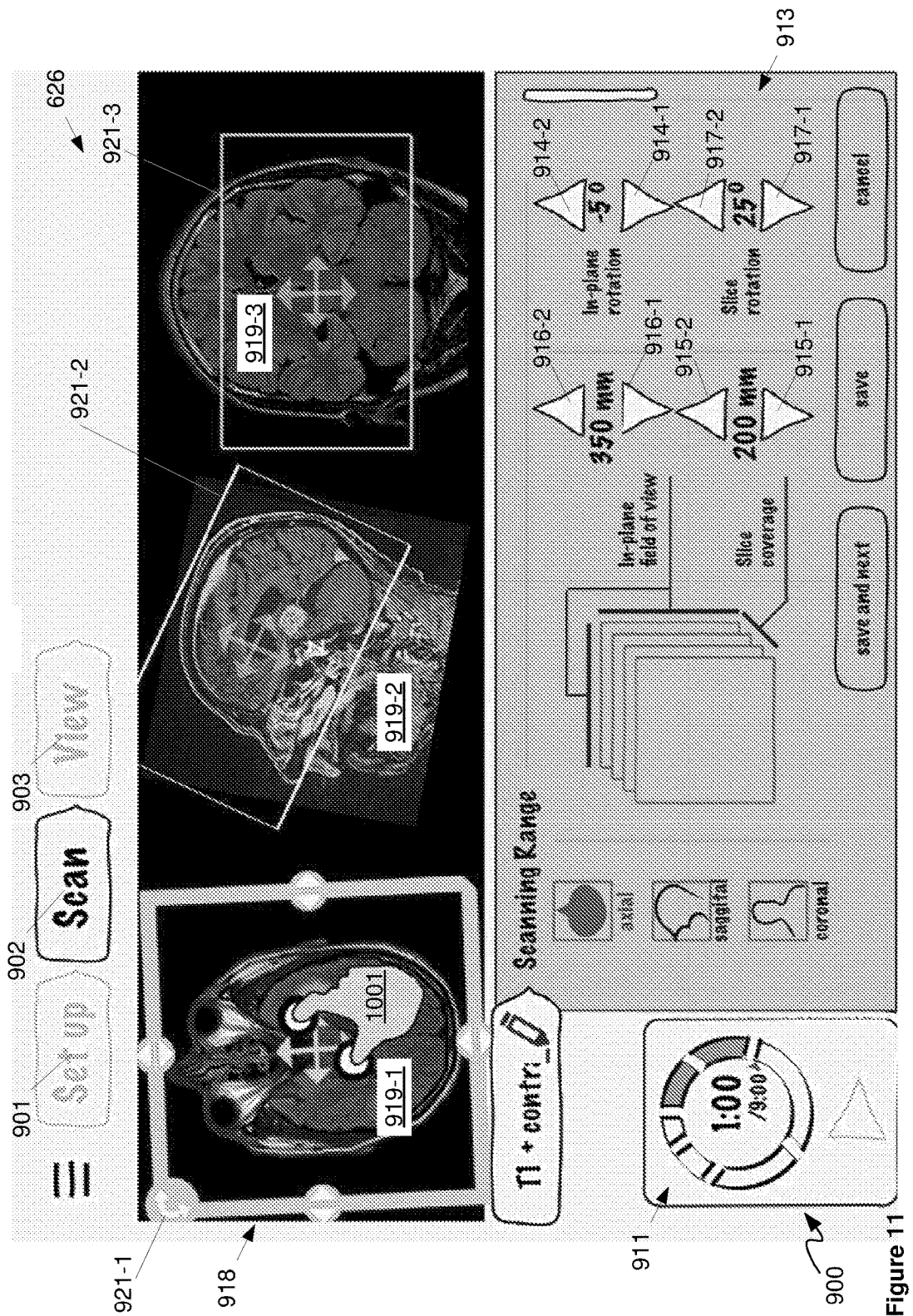
FIG. 11 depicts the GUI of FIG. 8 in which another representation of a selection of another scout scan is reoriented, according to non-limiting implementations.
Figure 12:
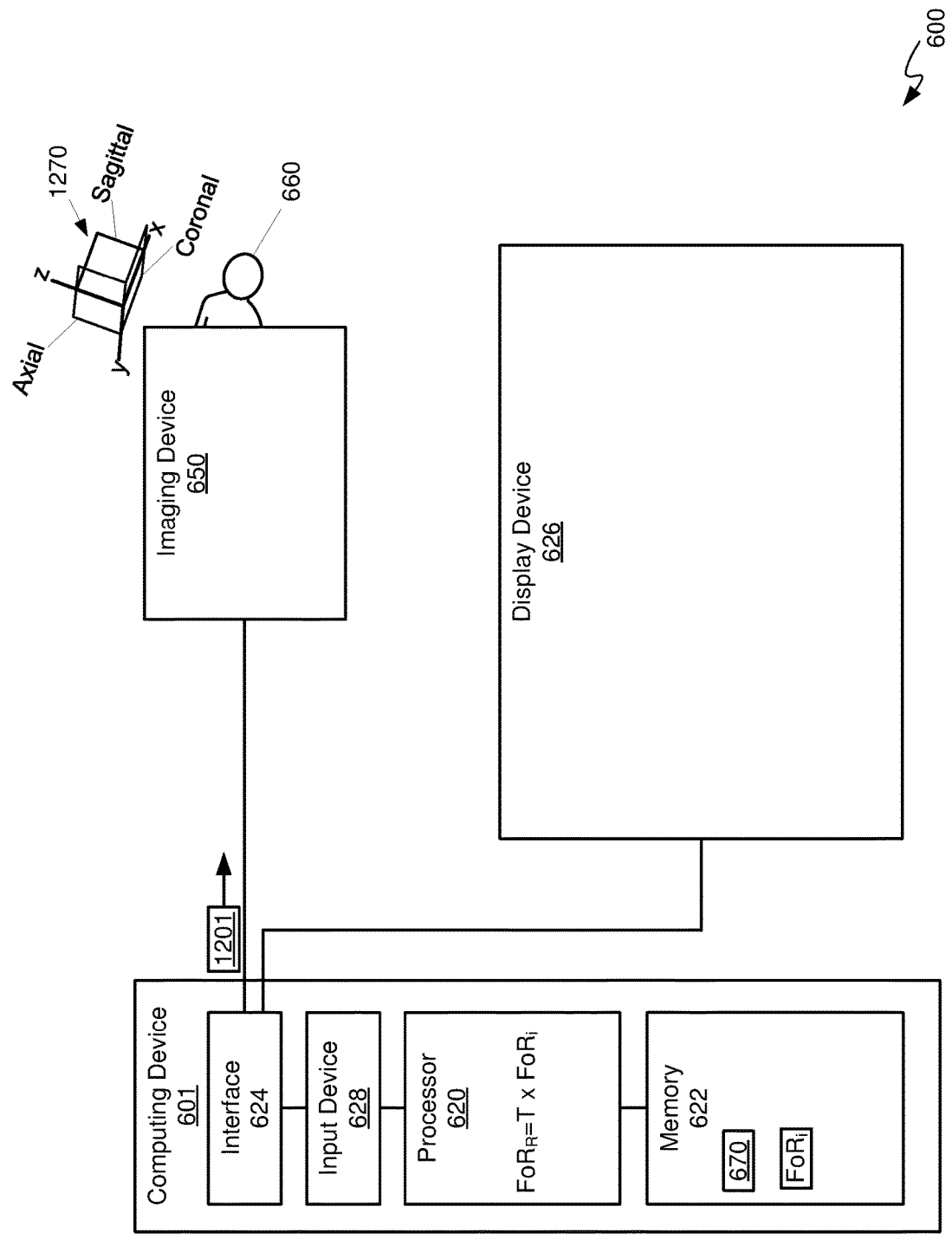
FIG. 12 depicts the system of FIG. 6, wherein a frame of reference is reoriented and an imaging device is instructed to acquire further images using the reoriented frame of reference, according to non-limiting implementations.

Similarly, in FIG. 11, hand 1001 interacts with the touchscreen of display device 626 to reorient selection 921-1. In particular, selection 921-1 is rotated; the degree of rotation is also reflected at controls 914 where the in-plane rotation, in FIG. 11, is 5° as compared to FIGS. 8 to 10, where the in-plane rotation is 0°.

While not depicted, selection 921-3 may also be reoriented, similar to how selections 921-1, 921-2 are reoriented.

Hence, the respective rectangles are again rendered, at display device 626, when input indicating the respective reorientation of one or more of selections 921 is received, for example when the respective rectangles are reoriented using the touchscreen.

Furthermore, while reorientation of selections 921 specifically occurs via touchscreen of display device 626, controls 914, 915, 916, 917 may also be used to reorient selections 921.

In particular, reoriented selections 921 represent both a reoriented frame of reference along which further images are to be acquired at imaging device 650, as well as an acquisition volume for acquiring further images.

For example, each of reoriented selections 921 may be representative of a respective side of a three-dimensional box within which the further images are to be acquired. Indeed, when each of selections 921 is reoriented at each of scans 919, the reorientation may be used to transform the initial frame of reference to produce a reoriented frame of reference; furthermore, the intersection of each of reoriented selections 921 represents a three-dimensional acquisition volume for the further images to be acquired by imaging device 650. Hence, when one or more of selections 921 is shifted and/or enlarged, even with rotation, the acquisition volume may also be shifted and/or enlarged.

Furthermore, while selections 921 are depicted as rectangles, in other implementations, selections 921 may be other shapes, for example squares, circles and the like. However, in general, an area of each selection 921 corresponds to an area to be scanned in further images to be acquired by imaging device 650.

In any event, GUI 900 generally conveys the relationship between the underlying anatomy and the surface of the anatomy of a patient to be scanned using imaging device 650, and by reorienting selections 921 using, for example, a multitouch input device, such as a touch screen, and/or another input device, the relationship between a scan orientation for further scans and the underlying anatomy may also be easily and conveniently prescribed.

For example, attention is next directed to FIG. 12, substantially similar to FIG. 6, with like elements having like numbers, where it is assumed in FIG. 12 that blocks 801 to 807 of method 800 have been implemented. In particular, FIG. 12 depicts processor 620 implementing block 809 of method by transforming data FoRi, representative of FOR 670, using a transformation matrix T, to produce data $FoR_R$ representative of a reoriented frame of reference that is oriented according to the reoriented representations.

In addition, FIG. 12 depicts processor 620 and/or computing device 601, at block 911, transmitting instructions 1201 to imaging device 650 to instruct imaging device 650 to acquire further images based on the reoriented frame of reference. In other words, further images acquired by imaging device 650 are to be oriented according to reoriented frame of reference, FOR 1270, that is based on reoriented selections 921. For example FOR 1270 is reoriented with respect to initial frame of reference 670, and FOR 1270 corresponds to data $FoR_R$ representative of a reoriented frame of reference.

In other words, instructions 1201 for acquiring the further images comprise instructions for acquiring a three-dimensional image oriented according to the reoriented frame of reference 1270. Such instructions 1201 may include instructions for reorienting and/or changing an acquisition volume according to the reoriented frame of reference 1270.

In particular, when imaging device 650 comprises a magnetic resonance imaging system, and processor 620 is further configured to instruct imaging device 650 to acquire the further images by instructing imaging device 650 to align magnetic gradients with reoriented frame of reference 1270.

Attention is next directed to FIGS. 13 to 17, each depicting an alternative GUI 1300, substantially similar to GUI 900 with like elements having like numbers. However, in GUI 1300 it is assumed that a three-dimensional scout scan has occurred and each of scans 919 were extracted therefrom.

Figure 13:
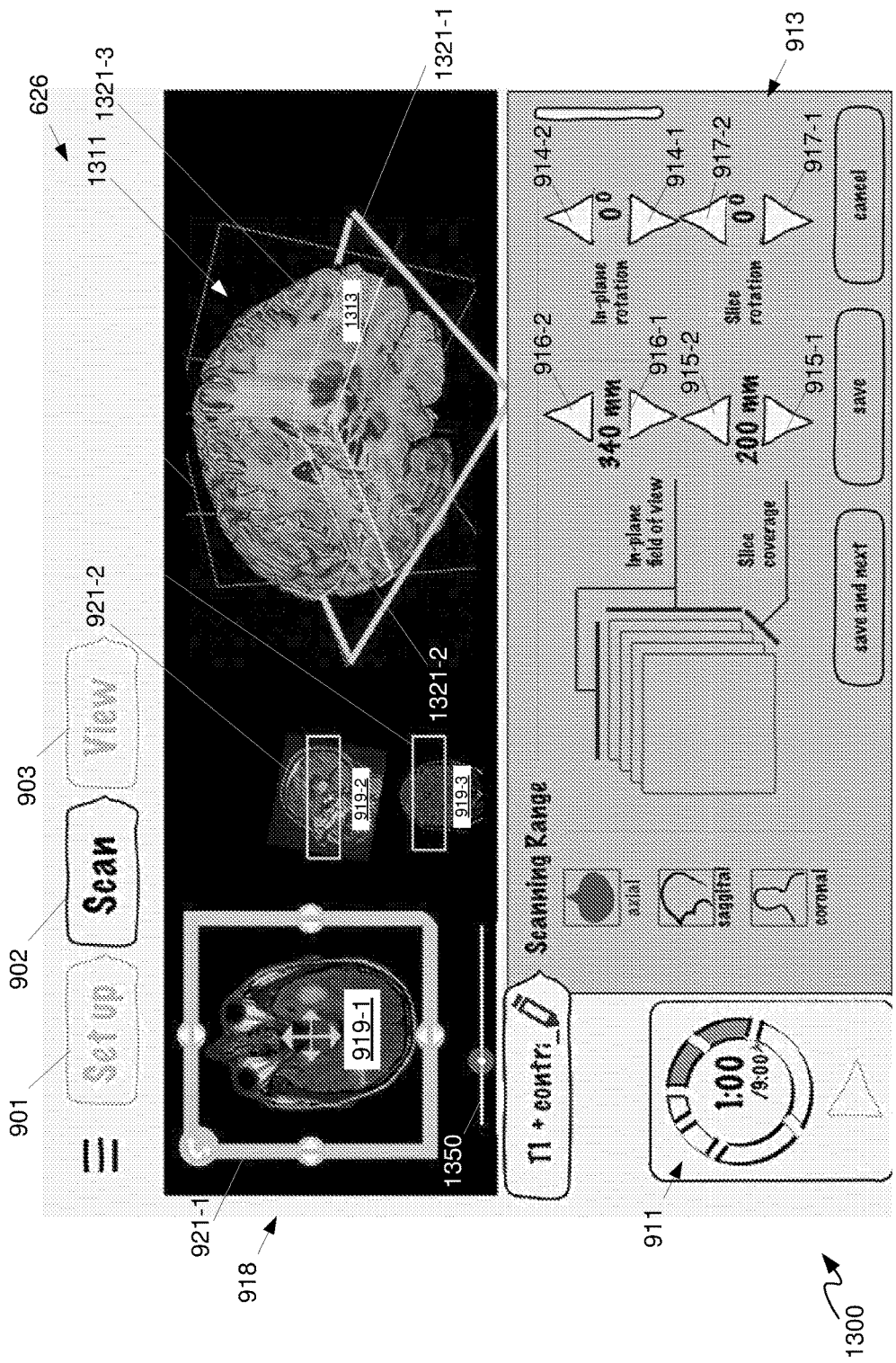
FIG. 13 depicts an alternative GUI for determining a scan orientation in the medical imaging system of FIG. 6, according to non-limiting implementations.

Furthermore, with reference to FIG. 13, it is assumed that processor 620 has processed the three-dimensional scout scan to produce a cut-out view 1311; and render, at display device 626, cut-out view 1311 combined with a three-dimensional volume representation 1313 of an acquisition volume.

As in GUI 900, each of selections 921 comprise automatically selected initial respective selections of a portion of each of scans 919, oriented according to the initial frame of reference. Cut-out view 1311 comprises: a representation of the three-dimensional scout scan (e.g. a brain of patient 660 is depicted in three dimensions) as well as indications of fields of view 1321-1, 1321-2, 1321-3, each respectively corresponding to scans 919-1, 919-2, 919-2. Fields of view 1321-1, 1321-2, 1321-3 will be interchangeably referred to hereafter, collectively, as fields of view 1321 and, generically, as a field of view 1321. Specifically, each of field of view 1321 is of a similar shape and a similar respective size as respective selections 921. Indeed, in these implementations, each of scans 919 is extracted from the three-dimensional scout scan along a plane represented by a respective field of view 1321. Hence, as depicted, each of fields of view 1321 comprises a rectangle overlaid on the three-dimensional representation of the three-dimensional scout scan at a same relative position and relative size as each of selections 921.

In particular, in cut-out view 1311, cut-away views of the three-dimensional scout scan are depicted along each of fields of view 1321.

Furthermore, three-dimensional volume representation 1313 of the acquisition volume corresponds to a volume defined by each of fields of view 1321, assuming that each field of view 321 represents a side of the acquisition volume.

Hence, cut-out view 1311 provides a "preview" of what a resulting scan slice will look like when the given three-dimensional acquisition volume is prescribed for the acquisition of further images. Indeed, GUI 1300 generally conveys the relationship between the underlying anatomy and the surface of the anatomy of a patient to be scanned using imaging device 650.

GUI 1300 further comprises a slider input 1350 described in more detail below with respect to FIGS. 16 and 17.

In any event, one or more of selections 921 may be reoriented similar to as-depicted in FIGS. 9 to 11, which results in a reorientation of a frame of reference as described above. Reorientation of selections 921 can also result in a reorientation of representation 1313 of the acquisition volume; alternatively, a size of one or more of selections 921 may be changed with respect to a respective scan 919 and/or a position of one or more of selections 921 may be changed with respect to a respective scan 919, which also results in a change in size and/or position of representation 1313 of the acquisition volume.

Figure 14:
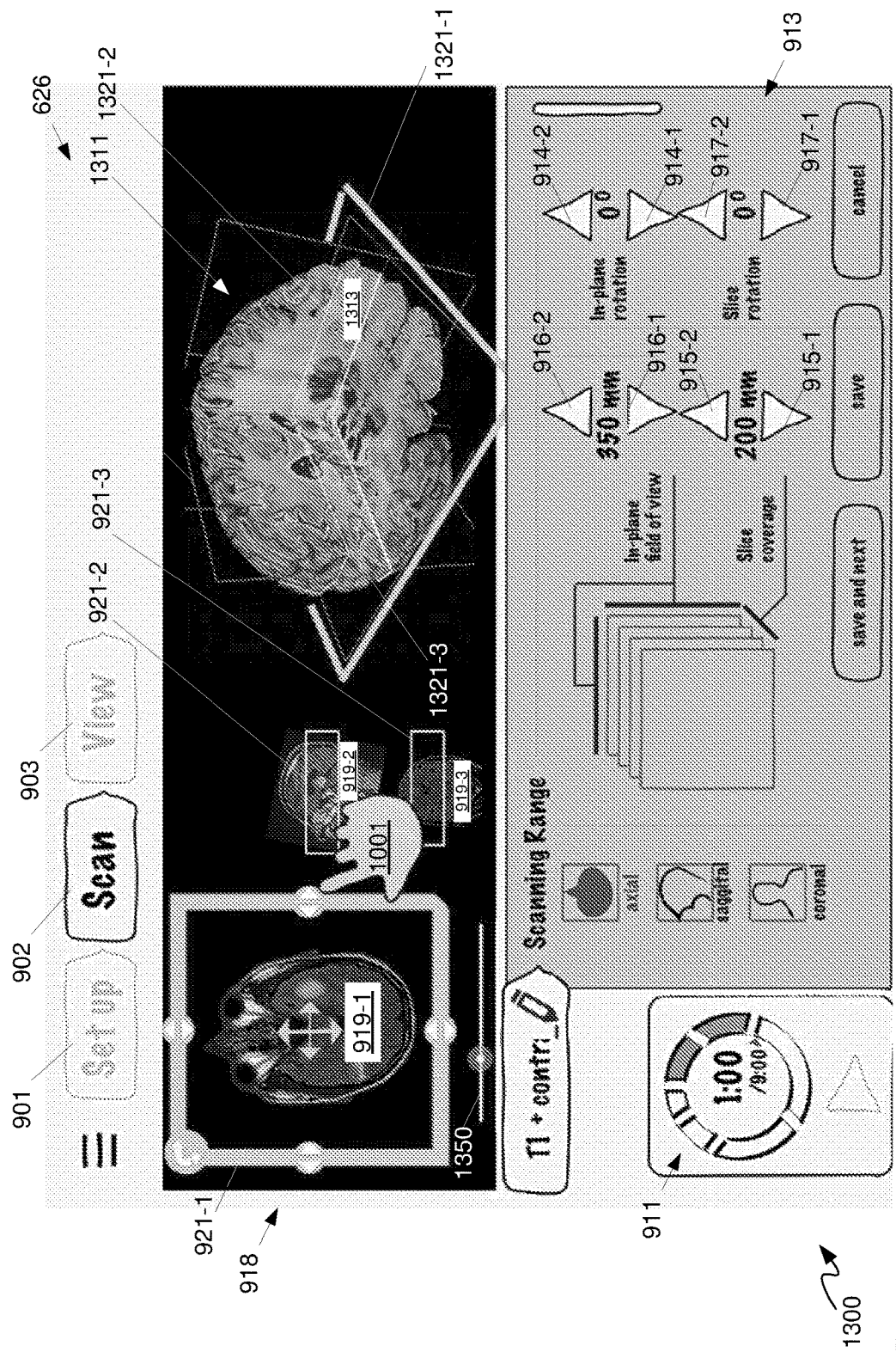
FIG. 14 depicts the GUI of FIG. 13 in which a representation of a selection of a scout scan is adjusted, according to non-limiting implementations.

For example, attention is directed to FIG. 14 where hand 1001 is depicted as enlarging selection 921-1, as compared to FIG. 13, which results in field of view 1321-1 being enlarged, and hence the representation 1313 of the acquisition volume is also enlarged; in some of these implementations, the acquisition volume of further images to be acquired at imaging device 650 is also enlarged.

It is further appreciated that, in FIGS. 13 and 14, scan 919-1 is depicted as larger than each of scans 919-2, 919-3, as scan 919-1 has been selected for interaction therewith. However, others of scans 919 may be selected for interaction, for example by hand 1001 selecting others of scans 919.

Figure 15:
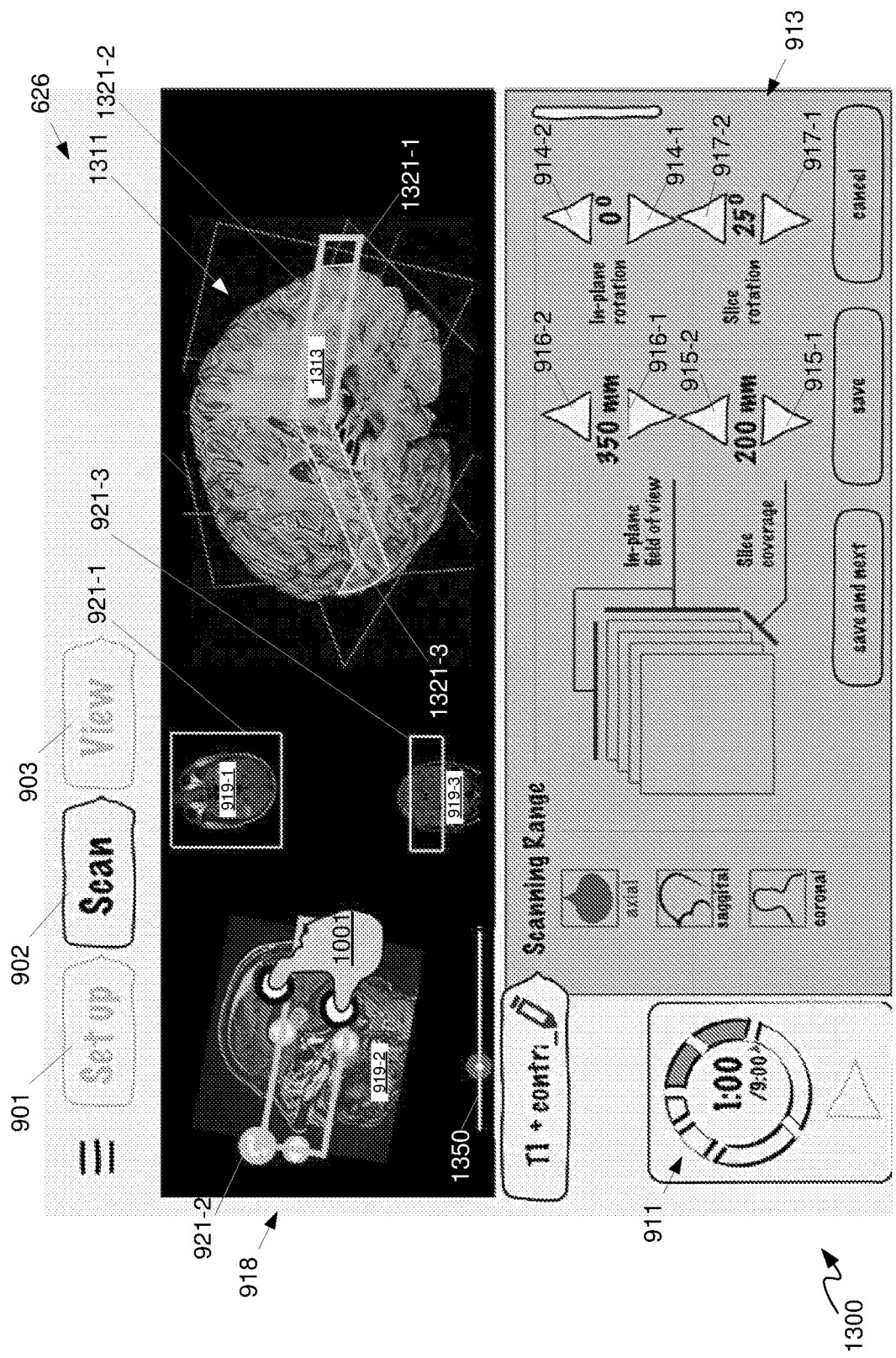
FIG. 15 depicts the GUI of FIG. 13 in which a representation of a selection of a scout scan is reoriented, according to non-limiting implementations.

Hence, attention is directed to FIG. 15 where it is assumed that scan 919-2 has been selected for interaction therewith and hence GUI 1300 has been reconfigured so that scan 919-2 is larger than scans 919-1, 919-3 and further scans 919 have been rearranged to emphasize scan 919-2. However, in other implementations, scans 919 may be the same size and need not be rearranged regardless of which of scans 919 is selected. Furthermore, as each of scans 919 is selected and/or rearranged and/or resized, respective selections 921 are also selected and/or rearranged and/or resized. The indication of fields of view 1321-1 has also been reemphasized at display device 626 as it is assumed that interaction with scan 919-1 is not to presently occur, at least until scan 919-1 is again selected.

In FIG. 15, selection 921-2 is reoriented via hand 1001 interacting with the touchscreen of display device 626, similar to reorientation of selection 921-2 in FIG. 10. The reorientation is correspondingly indicated in representation 1313 of acquisition volume, as well as by reorientation of field of view 1321-2. Reorienting of selection 921-2 may also result in a reorientation of the acquisition volume for further images acquired by imaging device 650. The orientation is also indicated in the slice rotation between controls 917.

Figure 16:
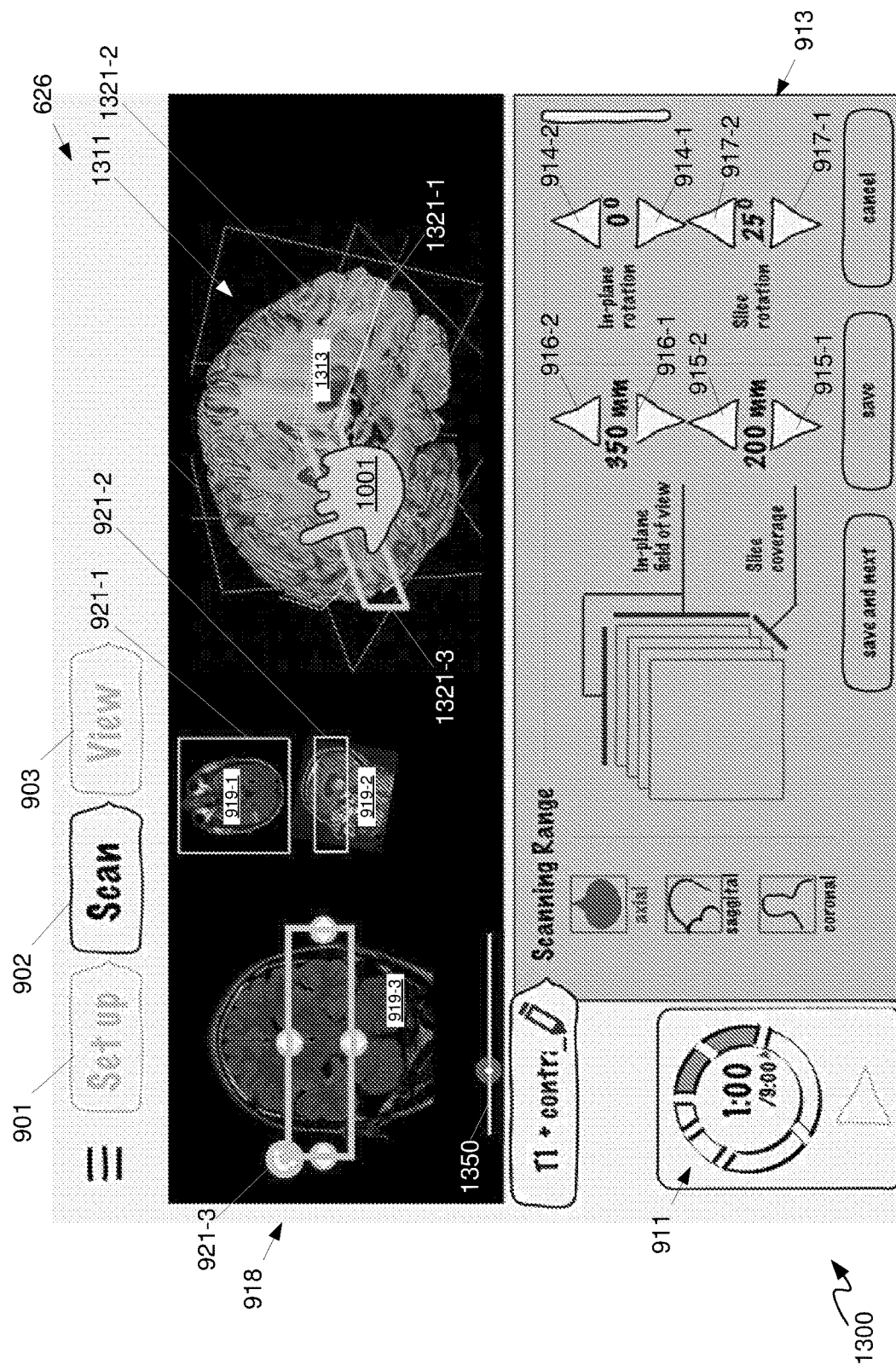
FIG. 16 depicts the GUI of FIG. 13 in which another scout scan is selected, according to non-limiting implementations.
Figure 17:
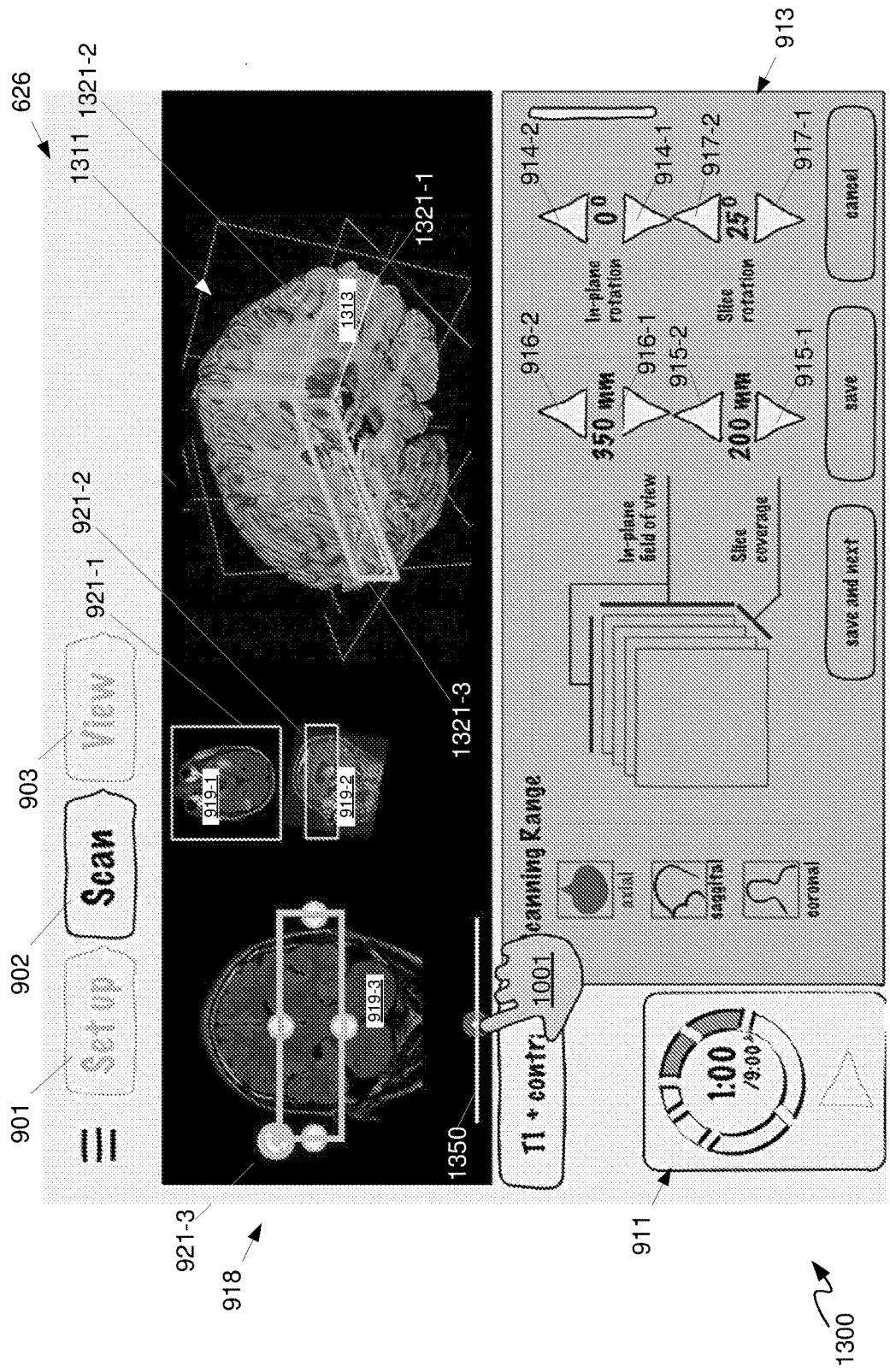
FIG. 17 depicts the GUI of FIG. 13 in which a cut-out view is adjusted, according to non-limiting implementations.

Attention is next directed to FIGS. 16 to 17 which depicts a further alternative feature of GUI 1300: scan 919-3 is selected via hand 1001 interacting with cut-out view 1311 using the touchscreen of display device 626, and specifically by selecting field of view 1321-3 corresponding to scan 919-3. As with scan 919-2 in FIG. 15, scan 919-3 is selected and scans 919 are reorganized, as are selections 921.

As depicted in FIG. 17, hand 1001 adjusts with slider input 1350, which results in field of view 1321-3 moving position (e.g. compare position of the slider of slider input 1350 in FIGS. 16 and 17), which is also reflected in representation 1313 of the acquisition volume position (e.g. compare size of representation 1313 in FIGS. 16 and 17). In some implementations, such adjustment may also result adjustment of the acquisition volume in future images to be acquired by imaging device 650.

In any event, the implementations described with reference to FIGS. 13 to 17 may results in a reorientation of FOR 670 to produce a transformed and/or reoriented FOR 670, as described above.

In any event, described herein is a medical imaging system for determining a scan orientation in which a frame of reference of further scans is determined from a reorienting of selections of scout scans rendered at a display device. Present implementations provide an easy and time saving method of conveying the relationship between the underlying anatomy and the surface of the anatomy, visualizing a field of view as a three-dimensional acquisition volume (e.g. as a three-dimensional slab), and intuitively manipulating and prescribing of the three-dimensional acquisition volume, for example, via multi-touch user interface such as a touchscreen.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A medical imaging system for determining a scan orientation, the medical imaging system comprising:
   a computing device comprising a processor, a communication interface and a memory;
   a display device;
   an input device configured to provide interactions with the display device; and,
   a magnetic resonance imaging system configured to acquire digital images,
   the computing device configured to communicate with the display device and the magnetic resonance imaging system using the communication interface, the processor configured to:
   instruct the magnetic resonance imaging system to acquire at least a sagittal scout scan, an axial scout scan and a coronal scout scan, based on an initial frame of reference, wherein magnetic gradients of the magnetic resonance imaging system are oriented with respect to the initial frame of reference such that the magnetic gradients are in a direction of a sagittal plane, an axial plane and a coronal plane the when sagittal scout scan, the axial scout scan and the coronal scout scan are acquired, the initial frame of reference based on one or more of the magnetic resonance imaging system and a patient located in the magnetic resonance imaging system;
   receive, from the magnetic resonance imaging system, the sagittal scout scan, the axial scout scan and the coronal scout scan;
   render, at the display device: a two-dimensional representation of each of the sagittal scout scan, the axial scout scan and the coronal scout scan;
   render, at the display device, initial respective selections of a portion of each of the sagittal scout scan, the axial scout scan and the coronal scout scan, oriented according to the initial frame of reference, the initial respective selections representing an initial field of view of an acquisition volume of the magnetic resonance imaging system, the initial respective selections being automatically selected according to the initial frame of reference;
   receive, from the input device, input indicating a respective reorientation of one or more of the initial respective selections;
   transform the initial frame of reference using the respective reorientation of one or more of the respective initial respective selections to produce a reoriented frame of reference; and, instruct the magnetic resonance imaging system to: align the magnetic gradients with the reoriented frame of reference; and acquire further images based on the reoriented frame of reference.

2. The medical imaging system of claim 1, wherein the processor is further configured to instruct the magnetic resonance imaging system to acquire at least the sagittal scout scan, the axial scout scan and the coronal scout scan by instructing the magnetic resonance imaging system to acquire a three-dimensional scout scan based on the initial frame reference.

3. The medical imaging system of claim 2, wherein the processor is further configured to extract the two-dimensional representation of each of the sagittal scout scan, the axial scout scan and the coronal scout scan from the three-dimensional scout scan.

4. The medical imaging system of claim 2, wherein the processor is further configured to: process the three-dimensional scout scan to produce a cut-out view; and render, at the display device, the cut-out view combined with a three-dimensional volume representation of the acquisition volume.

5. The medical imaging system of claim 1, wherein the processor is further configured to instruct the magnetic resonance imaging system to acquire at least the sagittal scout scan, the axial scout scan and the coronal scout scan by instructing the magnetic resonance imaging system to acquire a two-dimensional sagittal scout scan, a two-dimensional axial scout scan and a two-dimensional coronal scout scan.

6. The medical imaging system of claim 1, further comprising a device configured to acquire a patient frame of reference of the patient located in the magnetic resonance imaging system, the processor in communication with the device, and the initial frame of reference based on the patient frame of reference.

7. The medical imaging system of claim 1, wherein the automatically selected initial respective selections of a portion of each of the sagittal scout scan, the axial scout scan and the coronal scout scan comprise at least one three-dimensional selection.

8. The medical imaging system of claim 1, wherein instructions for acquiring the further images comprise instructions for acquiring a three-dimensional image oriented according to the reoriented frame of reference.

9. The medical imaging system of claim 1, wherein the initial respective selections comprise respective rectangles overlaid on each of the sagittal scout scan, the axial scout scan and the coronal scout scan.

10. The medical imaging system of claim 9, wherein the respective rectangles are again rendered, at the display device, when input indicating the respective reorientation of one or more of the initial respective selections is received.

11. The medical imaging system of claim 1, wherein the input device comprises one or more of: a touchscreen at the display device, a mouse, a rotatable mouse, a foot pedal, a microphone configured to receive voice commands, and a gesture-based input device.

12. The medical imaging system of claim 1, wherein the processor is further configured to render, at the display device, a three-dimensional volume representation of the acquisition volume based on the respective reorientation of one or more of the initial respective selections.

13. A method for determining a scan orientation, in a medical imaging system comprising:

at the medical imaging system comprising: a computing device comprising a processor, a communication interface and a memory; a display device; an input device configured to provide interactions with the display device; and, a magnetic resonance imaging system configured to acquire digital images, the computing device configured to communicate with the display device and the magnetic resonance imaging system using the communication interface:

instructing, at the processor, the magnetic resonance imaging system to acquire at least a sagittal scout scan, an axial scout scan and a coronal scout scan, based on an initial frame of reference, wherein magnetic gradients of the magnetic resonance imaging system are oriented with respect to the initial frame of reference such that the magnetic gradients are in a direction of a sagittal plane, an axial plane and a coronal plane the when sagittal scout scan, the axial scout scan and the coronal scout scan are acquired, the initial frame of reference based on one or more of the magnetic resonance imaging system and a patient located in the magnetic resonance imaging system;

receiving, at the processor, from the magnetic resonance imaging system, the sagittal scout scan, the axial scout scan and the coronal scout scan;

rendering, using the processor, at the display device: a two-dimensional representation of each of the sagittal scout scan, the axial scout scan and the coronal scout scan;

rendering, using the processor, at the display device, initial respective selections of a portion of each of the sagittal scout scan, the axial scout scan and the coronal scout scan, oriented according to the initial frame of reference, the initial respective selections representing an initial field of view of an acquisition volume of the magnetic resonance imaging system, the initial respective selections being automatically selected according to the initial frame of reference;

receiving, at the processor, from the input device, input indicating a respective reorientation of one or more of the initial respective selections;

transforming, at the processor, the initial frame of reference using the respective reorientation of one or more of the respective initial respective selections to produce a reoriented frame of reference; and instructing, at the processor, the magnetic resonance imaging system to: align the magnetic gradients with the reoriented frame of reference; and acquire further images based on the reoriented frame of reference.

14. The method of claim 13, further comprising instructing, at the processor, the magnetic resonance imaging system to acquire at least the sagittal scout scan, the axial scout scan and the coronal scout scan by instructing the magnetic resonance imaging system to acquire a three-dimensional scout scan based on the initial frame reference.

15. The method of claim 14, further comprising extracting, at the processor, the two-dimensional representation of each of the sagittal scout scan, the axial scout scan and the coronal scout scan from the three-dimensional scout scan.

16. The method of claim 14, further comprising: processing, at the processor, the three-dimensional scout scan to produce a cut-out view; and rendering, at the display device, the cut-out view combined with a three-dimensional volume representation of the acquisition volume.

17. The method of claim 13, further comprising instructing, at the processor, the magnetic resonance imaging system to acquire at least the sagittal scout scan, the axial scout scan and the coronal scout scan by instructing the magnetic resonance imaging system to acquire a two-dimensional sagittal scout scan, a two-dimensional axial scout scan and a two-dimensional coronal scout scan.

18. The method of claim 13, wherein the medical imaging system further comprises a device configured to acquire a patient frame of reference of the patient located in the magnetic resonance imaging system, the processor in communication with the device, and the initial frame of reference based on the patient frame of reference.

19. The method of claim 13, wherein the automatically selected initial respective selections of a portion of each of the sagittal scout scan, the axial scout scan and the coronal scout scan comprise at least one three-dimensional selection.

20. The method of claim 13, wherein instructions for acquiring the further images comprise instructions for acquiring a three-dimensional image oriented according to the reoriented frame of reference.

21. The method of claim 13, wherein the initial respective selections comprise respective rectangles overlaid on each of the sagittal scout scan, the axial scout scan and the coronal scout scan.

22. The method of claim 21, wherein the respective rectangles are again rendered, at the display device, when input indicating the respective reorientation of one or more of the initial respective selections is received.

23. The method of claim 13, further comprises rendering, at the display device, a three-dimensional volume representation of the acquisition volume based on the respective reorientation of one or more of the initial respective selections.

24. A non-transitory computer-readable medium storing a computer program, wherein execution of the computer program is for:
at a medical imaging system comprising: a computing device comprising a processor, a communication interface and a memory; a display device; an input device configured to provide interactions with the display device; and, an magnetic resonance imaging system configured to acquire digital images, the computing device configured to communicate with the display device and the magnetic resonance imaging system using the communication interface:
instructing, at the processor, the magnetic resonance imaging system to acquire at least a sagittal scout scan, an axial scout scan and a coronal scout scan, based on an initial frame of reference, wherein magnetic gradients of the magnetic resonance imaging system are oriented with respect to the initial frame of reference such that the magnetic gradients are in a direction of a sagittal plane, an axial plane and a coronal plane the when sagittal scout scan, the axial scout scan and the coronal scout scan are acquired, the initial frame of reference based on one or more of the magnetic resonance imaging system and a patient located in the magnetic resonance imaging system;
receiving, at the processor, from the magnetic resonance imaging system, the sagittal scout scan, the axial scout scan and the coronal scout scan;
rendering, using the processor, at the display device: a two-dimensional representation of each of the sagittal scout scan, the axial scout scan and the coronal scout scan;
rendering, using the processor, at the display device, initial respective selections of a portion of each of the sagittal scout scan, the axial scout scan and the coronal scout scan, oriented according to the initial frame of reference, the initial respective selections representing an initial field of view of an acquisition volume of the magnetic resonance imaging system, the initial respective selections being automatically selected according to the initial frame of reference;
receiving, at the processor, from the input device, input indicating a respective reorientation of one or more of the initial respective selections;
transforming, at the processor, the initial frame of reference using the respective reorientation of one or more of the respective initial respective selections to produce a reoriented frame of reference; and,
instructing, at the processor, the magnetic resonance imaging system to: align the magnetic gradients with the reoriented frame of reference; and acquire further images based on the reoriented frame of reference.

* * * * *